United States Patent [19]

Nagai et al.

[11] Patent Number: 4,614,819
[45] Date of Patent: Sep. 30, 1986

[54] NOVEL PROCESS FOR PRODUCING CEPHALOSPORINS

[75] Inventors: Takashi Nagai; Hirokazu Ochiai, both of Toyama; Takihiro Inaba, Namerikawa; Isao Myokan, Toyama; Hiroshi Sadaki, Tokyo; Isamu Saikawa, Toyama, all of Japan

[73] Assignee: Toyama Chemical Co., Ltd., Tokyo, Japan

[21] Appl. No.: 652,012

[22] Filed: Sep. 19, 1984

[30] Foreign Application Priority Data

Sep. 20, 1983 [JP] Japan ................. 58-172254

[51] Int. Cl.$^4$ .................. C07D 501/22; C07D 501/24; C07D 501/36
[52] U.S. Cl. .................... 540/222; 540/225; 540/227; 540/228
[58] Field of Search ........ 544/22, 25, 27, 28

[56] References Cited

U.S. PATENT DOCUMENTS 4,299,829 11/1981 Kamiya ................. 544/22
4,307,116 12/1981 Farge et al. ............ 544/27
4,385,181 5/1983 Farge et al. ........... 544/182
4,425,341 1/1984 Takaya et al. .......... 544/22
4,460,582 7/1984 Naylor ................. 544/22
4,489,072 12/1984 Sadaki et al. .......... 544/22

FOREIGN PATENT DOCUMENTS 8102083 3/1981 South Africa .
2089339 6/1982 United Kingdom .
2131800 6/1984 United Kingdom .

OTHER PUBLICATIONS

Fieser "Reagents for Organic Synthesis", vol. 6, 1977, p. 67.

Primary Examiner—Donald G. Daus
Assistant Examiner—Robert Benson
Attorney, Agent, or Firm—Oblon, Fisher, Spivak, McClelland & Maier

[57] ABSTRACT

This invention relates to a novel process for producing a useful cephalosporin which comprises reacting a thiolo ester compound with a 7-aminocephalosporin in the presence of boron trifluoride or a complex compound thereof. This process enables the cephalosporin to be produced with a high purity in a high yield.

8 Claims, No Drawings

NOVEL PROCESS FOR PRODUCING CEPHALOSPORINS

This invention relates to a novel process for producing cephalosporins.

Although various condensation reactions between a thiolo ester compound and a 7-aminocephalosporin have heretofore been known, all of them are only reactions between the 7-aminocephalosporin and an active thiolo ester compound having a heterocyclic thio group [Japanese Patent Application Kokai (Laid-Open) Nos. 154,980/80, 152,488/81 and 73,086/81 etc.]. On the other hand, the compound used in this invention represented by the formula:

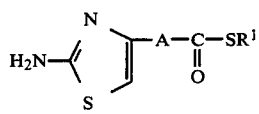

wherein $R^1$ is a substituted or unsubstituted alkyl, aralkyl or aryl group, and —A— is a methylene group or a group represented by the formula,

in which $R^2$ is a hydrogen atom; a substituted or unsubstituted alkyl, alkenyl, alkynyl, cycloalkyl, cycloalkenyl, aralkyl, aryl or heterocyclic group; a hydroxyl-protecting group; or a group represented by the formula,

(in which $R^3$ and $R^4$, which may be the same or different, are hydroxyl, alkyl, aralkyl, aryl, alkoxy, aralkyloxy or aryloxy groups), and the bond ∼ represents a syn- or anti-isomer or a mixture thereof], is very poor in reactivity, and therefore, it is substantially impossible to obtain the objective compound by some of the methods disclosed in the above-mentioned Japanese publications.

An object of this invention is to provide a process for producing a useful cephalosporin represented by the following formula [I] or a salt thereof by reacting a compound represented by the following formula [II] with a compound represented by the following formula [III] in the presence of boron trifluoride or a complex compound thereof.

A further object of this invention is to provide a process for producing a useful cephalosporin with a high purity in a high yield.

A still further object of this invention is to provide a process for producing a useful cephalosporin from the starting compounds which are inexpensive and easily available.

Other objects and advantages of this invention will be apparent from the following description.

According to this invention, there is provided a process for producing a cephalosporin represented by the formula [I] or a salt thereof:

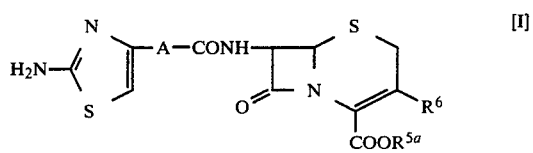

wherein $R^{5a}$ is a hydrogen atom or a carboxyl-protecting group; $R^6$ is a hydrogen atom, a halogen atom, a lower alkyl group or a group represented by the formula, —$CH_2R^7$ in which $R^7$ is a hydroxyl group or a substituted or unsubstituted acyloxy, carbamoyloxy, acylamino, aryl, heterocyclic thio, aromatic heterocyclic or heterocyclic group, said aromatic heterocyclic group being attached to the exomethylene group at the 3-position of the cephem ring through a carbon-carbon bond, and said heterocyclic group being attached to the exomethylene group at the 3-position of the cephem ring through a carbon-nitrogen bond; and —A— is a methylene group or a group represented by the formula

[in which $R^2$ is a hydrogen atom; a substituted or unsubstituted alkyl, alkenyl, alkynyl, cycloalkyl, cycloalkenyl, aralkyl, aryl or heterocyclic group; a hydroxyl-protecting group; or a group represented by the formula,

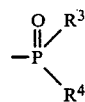

(in which $R^3$ and $R^4$, which may be the same or different, are hydroxyl, alkyl, aralkyl, aryl, alkoxy, aralkyloxy or aryloxy groups), and the bond ∼ represents a syn- or anti-isomer or a mixture thereof], which comprises reacting a compound represented by the formula [II]:

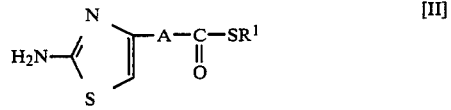

wherein —A— has the same meaning as defined above, and $R^1$ is a substituted or unsubstituted alkyl, aralkyl or aryl group, with a compound represented by the formula [III]:

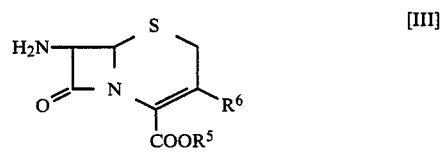

wherein $R^5$ represents a carboxyl-protecting group; and $R^6$ has the same meaning as defined above, in the presence of boron trifluoride or a complex compound thereof and then, if desired, removing the carboxyl-protecting group or converting the product to a salt.

The cephalosporin represented by the formula [I] or the salt thereof which are obtained by the process of this invention have a broad antibacterial spectrum, and also exhibit an excellent antibacterial activity against gram-positive and gram-negative bacteria and a good stability against β-lactamase produced by bacteria. Accordingly, the compound obtained by the process of this invention exhibits an excellent therapeutic effect on human and animal diseases through oral and parenteral administrations.

This invention will be further explained in detail below.

In this specification, unless otherwise specified, the term "alkyl" means a straight or branched chain $C_{1-14}$alkyl group, for example, methyl, ethyl, n-propyl, isopropyl, n-butyl, isobutyl, sec.-butyl, tert.-butyl, pentyl, hexyl, heptyl, octyl, dodecyl or the like; the term "alkenyl" means a $C_{2-10}$alkenyl group, for example, vinyl, allyl, isopropenyl, butenyl, 2-pentenyl or the like; the term "alkynyl" means a $C_{2-10}$ alkynyl group, for example, ethynyl, 2-propynyl or the like; the term "cycloalkyl" means a $C_{3-7}$cycloalkyl group, for example, cyclopropyl, cyclobutyl, cyclopentyl, cyclohexyl, cycloheptyl or the like; the term "cycloalkenyl" means a $C_{5-7}$cycloalkenyl group, for example, cyclopentenyl, cyclohexenyl, cycloheptenyl or the like; the term "aryl" means, for example, phenyl, tolyl, naphthyl, indanyl or the like; the term "aralkyl" means, for example, benzyl, phenethyl, 4-methylbenzyl, naphthylmethyl or the like; the term "acyl" means a $C_{1-12}$acyl group, for example, formyl, acetyl, propionyl, butyryl, pivaloyl, pentanecarbonyl, cyclohexanecarbonyl, benzoyl, naphthoyl, furoyl, thenoyl or the like; the term "heterocyclic group" means a heterocyclic group having at least one hetero atom selected from oxygen, sulfur and nitrogen atoms in the ring, for example, furyl, thienyl, pyrrolyl, pyrazolyl, imidazolyl, thiazolyl, isothiazolyl, oxazolyl, isoxazolyl, oxadiazolyl, triazolyl, tetrazolyl, thiadiazolyl, imidazolidinyl, imidazolinyl, pyrrolidinyl, pyrazolinyl, pyrrolinyl, thiatriazolyl, oxatriazolyl, indolyl, pyridyl, pyrimidinyl, pyridazinyl, pyrazinyl, pyranyl, piperazinyl, piperidyl, hexamethyleneimino, morpholinyl, triazinyl, benzothienyl, benzofuryl, benzoxazolyl, benzothiazolyl, purinyl, isobenzofuryl, isoindolyl, indazolyl, quinolizinyl, quinolyl, isoquinolyl or the like; and the term "halogen atom" means fluorine, chlorine, bromine, iodine or the like. Also, the term "lower" means 1 to 5 carbon atoms.

When in various terms used herein, there are, for example, alkyl, alkenyl, aryl, aralkyl, acyl, heterocyclic groups and the like, they have the same meanings as mentioned above unless otherwise specified.

In the present specification, the group —A— is a methylene group or a group represented by the formula,

[in which $R^2$ is a hydrogen atom; a substituted or unsubstituted alkyl, alkenyl, alkynyl, cycloalkyl, cycloalkenyl, aralkyl, aryl or heterocyclic group; a hydroxyl-protecting group; or a group represented by the formula,

(in which $R^3$ and $R^4$, which may be the same or different, are hydroxyl, alkyl, aralkyl, aryl, alkoxy, aralkyloxy or aryloxy groups), and the bond $\sim$ represents a syn- or anti-isomer or a mixture thereof].

In the above definition, the hydroxyl-protecting group includes all groups which can be usually used as protecting groups of a hydroxyl group, for example, easily removable acyl groups such as benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, 4-(phenylazo)benzyloxycarbonyl, 4-(4-methoxyphenylazo)benzyloxycarbonyl, tert.-butoxycarbonyl, 1,1-dimethylpropoxycarbonyl, isopropoxycarbonyl, diphenylmethoxycarbonyl, 2,2,2-trichloroethoxycarbonyl, 2,2,2-tribromoethoxycarbonyl, 2-furfuryloxycarbonyl, 1-adamantyloxycarbonyl, 1-cyclopropylethoxycarbonyl, 8-quinolyloxycarbonyl, formyl, acetyl, (mono-, di- or tri-)chloroacetyl, benzoyl, trifluoroacetyl and the like; alkylsulfonyl groups such as methanesulfonyl, ethanesulfonyl and the like; arylsulfonyl groups such as phenylsulfonyl, toluenesulfonyl and the like; a benzyl group; a trityl group; a methoxymethyl group; a 2-nitrophenylthio group; a 2,4-dinitrophenylthio group; a tetrahydropyranyl group; a tetrahydrofuranyl group; and the like.

Furthermore, the substituents on the alkyl, alkenyl, alkynyl, cycloalkyl, cycloalkenyl, aralkyl, aryl or heterocyclic groups for $R^2$ include, for example, a halogen atom, an oxo group, a cyano group, a hydroxyl group, an alkoxy group, an amino group, an alkylamino group, a dialkylamino group, a heterocyclic group or a group represented by the formula,

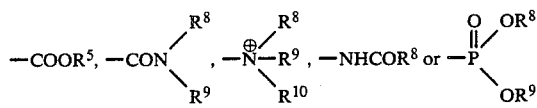

in which $R^5$ has the same meaning as defined above; and $R^8$, $R^9$ and $R^{10}$, which may be the same or different, are hydrogen atoms, alkyl, aralkyl or aryl groups or the like, and the above-mentioned groups for $R^2$ may be substituted by at least one of these substituents. Among these substituents, the hydroxyl or amino group may be protected with one of the above-mentioned hydroxyl-protecting groups or the amino-protecting groups which will be mentioned below.

The amino-protecting groups include all groups which can be usually used as amino-protecting groups, for example, easily removable acyl groups such as 2,2,2-trichloroethoxycarbonyl, 2,2,2-tribromoethoxycarbonyl, benzyloxycarbonyl, p-toluenesulfonyl, 4-nitrobenzyloxycarbonyl, 4-bromobenzyloxycarbonyl, (mono-, di- or tri-)chloroacetyl, trifluoroacetyl, formyl, tert.-amyloxycarbonyl, tert.-butoxycarbonyl, 4-methoxybenzyloxycarbonyl, 3,4-dimethoxybenzyloxycarbonyl, 4-(phenylazo)benzyloxycarbonyl, 4-(4-methoxyphenylazo)benzyloxycarbonyl, (pyridine-1-oxide-2- yl)methoxycarbonyl, 2-furfuryloxycarbonyl, diphenylmethoxycarbonyl, 1,1-dimethylpropoxycarbonyl, isopropoxycarbonyl, 1-cyclopropylethoxycarbonyl, phthaloyl, succinyl, 1-adamantyloxycarbonyl, 8-quinolyloxycarbonyl and the like; easily removable groups such as trityl, 2-nitrophenylthio, 2,4-dinitrophenylthio, 2-hydroxybenzylidene, 2-hydroxy-5-chlorobenzylidene, (2-hydroxynaphthalene-1-yl)methyl, (3-hydroxypyridine-4-yl)methyl, 1-methoxycarbonyl-2-propylidene, 1-ethoxycarbonyl-2-propylidene, 3-ethoxycarbonyl-2-butylidene, 1-acetyl-2-propylidene, 1-benzoyl-2-propylidene, 1-[N-(2-methoxyphenyl)carbamoyl]-2-propylidene, 1-[N-(4-methoxyphenyl)carbamoyl]-2-propylidene, 2-ethoxycarbonylcyclohexylidene, 2-ethoxycarbonylcyclopentylidene, 2-acetylcyclohexylidene, 3,3-dimethyl-5-oxocyclohexylidene and the like; a di- or tri-alkylsilyl group; and the like.

The group $R^1$ is a substituted or unsubstituted alkyl, aralkyl or aryl group, and the substituents thereon include, for example, a halogen atom, a nitro group, an oxo group, an alkyl group, an aralkyl group, an aryl group, an alkenyl group, a hydroxyl group, an alkoxy group, an alkylthio group, a cyano group, an amino group, an alkylamino group, a dialkylamino group, an acylamino group, an acyl group, an acyloxy group, an acylalkyl group, a carboxyl group, an alkoxycarbonyl group, an alkoxycarbonylalkyl group, a carbamoyl group, an aminoalkyl group, an N-alkylaminoalkyl group, an N,N-dialkylaminoalkyl group, a hydroxyalkyl group, a hydroxyiminoalkyl group, an alkoxyalkyl group, a carboxyalkyl group, a sulfoalkyl group, a sulfo group, a sulfamoylalkyl group, a sulfamoyl group, a carbamoylalkyl group, a carbamoylalkenyl group, an N-hydroxycarbamoylalkyl group and the like. The above-mentioned alkyl, aralkyl or aryl group for $R^1$ may be substituted by at least one of these substituents. Among these substituents, the hydroxyl group and the amino group may be protected with the hydroxyl-protecting group and the amino-protecting group, respectively, explained as to $R^2$, and the carboxyl group may be protected with a carboxyl-protecting group which will be mentioned as to $R^5$ and $R^{5a}$ below.

The carboxyl-protecting group for $R^5$ and $R^{5a}$ may be those which are conventionally used in the fields of penicillin and cephalosporin, and includes, for example, ester-forming groups which are readily removable on catalytic reduction, chemical reduction or treatment under other mild conditions, or ester-forming groups which are readily removable in living bodies.

As the preferable protecting groups among these protecting groups, the following are specifically mentioned:

(a) alkyl groups;

(b) substituted lower alkyl groups, at least one of the substituents of which is halogen, nitro, acyl, alkoxy, oxo, cyano, cycloalkyl, aryl, alkylsulfonyl, alkoxycarbonyl, 5-alkyl-2-oxo-1,3-dioxol-4-yl, 1-indanyl, 2-indanyl, furyl, pyridyl, 4-imidazolyl, phthalimido, succinimido, azetidino, aziridino, 1-pyrrolidinyl, piperidino, morpholino, thiomorpholino, N-lower alkyl-1-piperazinyl, pyrrolyl, pyrazolyl, thiazolyl, isothiazolyl, oxazolyl, isoxazolyl, thiadiazolyl, oxadiazolyl, thiatriazolyl, oxatriazolyl, triazolyl, tetrazolyl, quinolyl, phenazinyl, benzofuryl, benzothienyl, benzoxazolyl, benzothiazolyl, coumarinyl, 2,5-dimethyl-1-pyrrolidinyl, 1,4,5,6-tetrahydropyrimidinyl, 4-methylpiperidino, 2,6-dimethylpiperidino, 4-(5-methyl-2-pyrrolinyl), 4-(2-pyrrolinyl), N-methylpiperidinyl, 1,3-benzodioxolanyl, alkylamino, dialkylamino, acyloxy, acylthio, acylamino, dialkylaminocarbonyl, alkoxycarbonylamino, alkenyloxy, aryloxy, aralkyloxy, cycloalkyloxy, cycloalkenyloxy, heterocyclicoxy, alkoxycarbonyloxy, alkenyloxycarbonyloxy, aryloxycarbonyloxy, aralkyloxycarbonyloxy, heterocyclicoxycarbonyloxy, alkenyloxycarbonyl, aryloxycarbonyl, aralkyloxycarbonyl, cycloalkyloxycarbonyl, cycloalkenyloxycarbonyl, heterocyclicoxycarbonyl, alkylanilino, or alkylanilino substituted by halogen, lower alkyl or lower alkoxy;

(c) cycloalkyl groups, lower alkyl-substituted cycloalkyl groups or (2,2-di-lower alkyl-1,3-dioxol-4-yl)methyl groups;

(d) alkenyl groups;

(e) alkynyl groups;

(f) phenyl group, substituted phenyl groups, at least one of the substituents of which is arbitrarily selected from the substituents exemplified in above (b), or aryl groups such as groups represented by the formula:

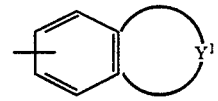

wherein $-Y^1-$ is $-CH=CH-O-$, $-CH=CH-S-$, $-CH_2CH_2S-$, $-CH=N-CH=N-$, $-CH=CH-CH=CH-$, $-CO-CH=CH-CO-$, or $-CO-CO-CH=CH-$, or substituted derivatives thereof, the substituents of which are arbitrarily selected from those exemplified in above (b), or groups represented by the formula:

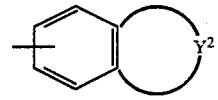

wherein $-Y^2-$ is a lower alkylene group such as $-(CH_2)_3-$ or $-(CH_2)_4-$ or the like, or substituted derivatives thereof, the substituents of which are arbitrarily selected from those exemplified in above (b);

(g) aralkyl groups such as benzyl or substituted benzyl, at least one of the substituents of which is arbitrarily selected from those exemplified in above (b);

(h) heterocyclic groups or substituted heterocyclic groups, at least one of the substituents of which is arbitrarily selected from those exemplified in above (b);

(i) alicyclic indanyl or alicyclic phthalidyl groups, methyl- or halogen-substituted derivatives thereof, alicyclic tetrahydronaphthyl groups, methyl- or halogen-substituted derivatives thereof, trityl, cholesteryl, bicyclo[4,4,0]decyl and the like; and (j) alicyclic phthalidylidene-lower alkyl groups or halogen- or lower alkyl-substituted derivatives thereof.

The particularly preferable carboxyl-protecting groups among them include, for example, alkyl, aralkyl, diphenylmethyl, phthalidyl, acyloxyalkyl, acyloxyaralkyl and the like. As the acyloxyalkyl and acyloxyaralkyl groups, there are specifically mentioned, for example, acetoxymethyl, pivaloyloxymethyl, propionyloxymethyl, butyryloxymethyl, isobutyryloxymethyl, valeryloxymethyl, 1-acetoxyethyl, 1-acetoxy-n-propyl, 1-pivaloyloxyethyl, 1-pivaloyloxy-n-propyl, benzoyloxymethyl, 1-benzoyloxyethyl, α-pivaloyloxybenzyl, α-acetoxybenzyl and the like.

The group $R^6$ is a hydrogen atom, a halogen atom, a lower alkyl group or a group represented by the formula —$CH_2R^7$, in which $R^7$ is a hydroxyl group or a substituted or unsubstituted acyloxy, carbamoyloxy, acylamino, aryl or heterocyclicthio group, a substituted or unsubstituted aromatic heterocyclic group attached to the exomethylene group at the 3-position of the cephem ring through a carbon-carbon bond, or a substituted or unsubstituted heterocyclic group attached to the exomethylene group at the 3-position of the cephem ring through a carbon-nitrogen bond. The aromatic heterocyclic group attached to the exomethylene group at the 3-position of the cephem ring through a carbon-carbon bond includes, for example, thenyl, furyl and the like. Furthermore, the heterocyclic group attached to the exomethylene group at the 3-position of the cephem ring through a carbon-nitrogen bond includes, for example, tetrazolyl, triazoyl, (di- or tetra-hydro)pyrazinyl, (di- or tetra-hydro)pyridazinyl, dihydropyrimidinyl, and five- or six-membered cyclic groups represented by the formula,

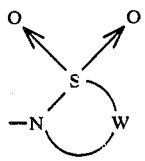

in which W is a divalent group, for example, 1,2,6-thiadiazine-1,1-dioxide-2-yl, isothiazolidine-1,1-dioxide-2-yl and the like. More specifically, said heterocyclic group includes 1-(1,2,3,4-tetrazolyl), 2-(1,2,3,4-tetrazolyl), 1-(1,2,3-triazolyl), 2-(1,2,3-triazolyl), 1-(1,2,4-triazolyl), 4-(1,2,4-triazolyl), 2,3-dioxo-1,2,3,4-tetrahydropyrazinyl, 3,6-dioxo-1,2,3,6-tetrahydropyridazinyl, 6-oxo-1,6-dihydropyridazinyl, 2-oxo-1,2-dihydropyrazinyl, 6-oxo-1,6-dihydropyrimidinyl, 2-oxo-1,2-dihydropyrimidinyl, 1,2,6-thiadiazine-1,1-dioxide-2-yl, isothiazolidine-1,1-dioxide-2-yl and the like.

Also, the substituents on the acyloxy, carbamoyloxy, acylamino, aryl and heterocyclicthio groups, the aromatic heterocyclic group attached to the exomethylene group at the 3-position of the cephem ring through a carbon-carbon bond, and the heterocyclic group attached to the exomethylene group at the 3-position of the cephem ring through a carbon-nitrogen bond for $R^7$ include the substitutents on the alkyl, aralkyl or aryl groups which have been explained as to $R^1$, and the above-mentioned groups for $R^7$ may be substituted by at least one of these substituents. Among these substituents, the hydroxyl group and the amino group may be protected with the hydroxyl-protecting group and the amino-protecting group, respectively, explained as to $R^2$, and the carboxyl group may be protected with the carboxyl-protecting group mentioned as to $R^5$ and $R^{5a}$.

The salts of the compound represented by the formula [I] include salts at the basic groups and the acidic groups which have conventionally been well-known in the fields of penicillin and cephalosporin. The salts at the basic groups include, for example, salts with mineral acids such as hydrochloric acid, nitric acid, sulfuric acid and the like; salts with organic carboxylic acids such as oxalic acid, succinic acid, formic acid, trichloroacetic acid, trifluoroacetic acid and the like; and salts with sulfonic acids such as methanesulfonic acid, ethanesulfonic acid, benzenesulfonic acid, toluene-2-sulfonic acid, toluene-4-sulfonic acid, mesitylenesulfonic acid(2,4,6-trimethylbenzenesulfonic acid), naphthalene-1-sulfonic acid, naphthalene-2-sulfonic acid, phenylmethanesulfonic acid, benzene-1,3-disulfonic acid, toluene-3,5-disulfonic acid, naphthalene-1,5-disulfonic acid, naphthalene-2,6-disulfonic acid, naphthalene-2,7-disulfonic acid, benzene-1,3,5-trisulfonic acid, benzene-1,2,4-trisulfonic acid, naphthalene-1,3,5-trisulfonic acid and the like. The salts at the acidic groups include, for example, salts with alkali metals such as sodium, potassium and the like; salts with alkaline earth metals such as calcium, magnesium and the like; ammonium salts; and salts with nitrogen-containing organic bases such as procaine, dibenzylamine, N-benzyl-$\beta$-phenethylamine, ephenamine, N,N-dibenzylethylenediamine, triethylamine, trimethylamine, tributylamine, pyridine, N,N-dimethylaniline, N-methylpiperidine, N-methylmorpholine, diethylamine, dicyclohexylamine and the like.

The process of this invention is explained below referring to the embodiments thereof.

This invention relates to a process for producing a cephalosporin represented by the formula [I] or a salt thereof by reacting the compound represented by the formula [II] with the compound represented by the formula [III] in the presence of boron trifluoride or a complex compound thereof and then, if desired, removing the carboxyl-protecting group or converting the product to a salt.

Complex compounds of boron trifluoride include, for example, complex compounds of boron trifluoride with dialkyl ethers such as diethyl ether, di-n-propyl ether, di-n-butyl ether and the like; complex compounds of boron trifluoride with carboxylic acid esters such as ethyl formate, ethyl acetate and the like; complex compounds of boron trifluoride with fatty acids such as acetic acid, propionic acid and the like; complex compounds of boron trifluoride with phenols such as phenol and the like; or complex compounds of boron trifluoride with nitriles such as acetonitrile, propionitrile and the like. Particularly preferable complex compounds include complex compounds of boron trifluoride with dialkyl ethers.

In this reaction, the use of an organic solvent is preferred. The organic solvent may be any organic solvent as far as it does not adversely affect the reaction, and include, for example, nitroalkanes such as nitromethane, nitroethane, nitropropane and the like; organic carboxylic acids such as formic acid, acetic acid, trifluoroacetic acid, dichloroacetic acid, propionic acid and the like; ethers such as diethyl ether, di-isopropyl ether, dioxane, tetrahydrofuran, ethylene glycol dimethyl ether, anisole and the like; esters such as ethyl formate, diethyl carbonate, methyl acetate, ethyl acetate, diethyl oxalate, ethyl chloroacetate, butyl acetate and the like; halogenated hydrocarbons such as methylene chloride, chloroform, 1,2-dichloroethane and the like; sulfolane; etc. and among them, the halogenated hydrocarbons are preferred. Also, these solvents may be used in admixture of two or more. Moreover, complex compounds of boron trifluoride with these organic solvents may be used as the solvent for the reaction. It is sufficient that the amount of boron trifluoride or a complex-compound thereof and the amount of the compound represented by the formula [II] used are 1 mole or more, preferably 1–5 moles, per mole of the compound represented by the formula [III].

The sequence of addition of the compounds represented by the formulae [II] and [III] and boron trifluoride or a complex compound thereof is not critical in this reaction; however it is preferable to mix the compound represented by the formula [II] with boron trifluoride or a complex compound thereof and then add the compound represented by the formula [III] to the above mixture.

Next, the processes for the production of the thiolo ester compound represented by the formula [II] will be explained below. This compound can be prepared, for example, according to the following production processes:

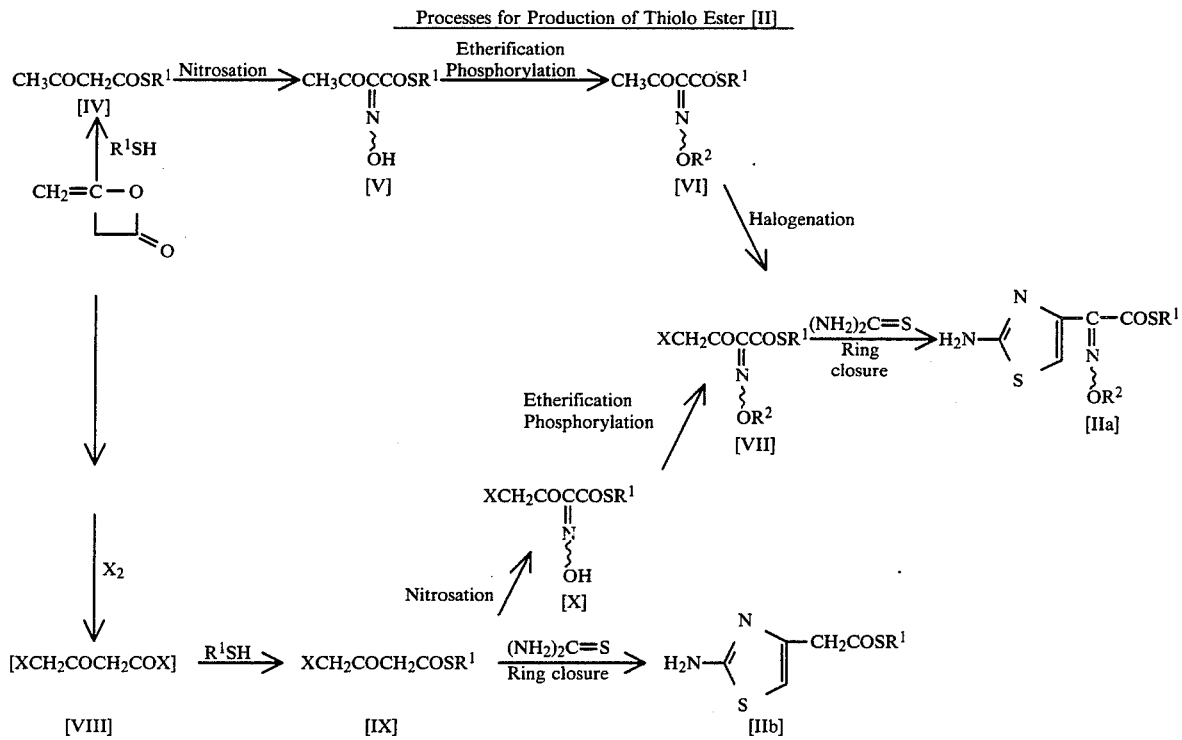

Processes for Production of Thiolo Ester [II]

The reaction is usually conducted at a temperature of 0°–100° C., and completed in several tens of minutes to several tens of hours. The presence of water in the reaction system may cause undesirable side reactions such as the ring cleavage of the β-lactam ring or the like, so that it is desirable to maintain the reaction system in the anhydrous state. An appropriate dehydrating agent such as anhydrous magnesium sulfate, molecular sieve or the like may be added to the reaction system for the purpose of satisfying said conditions.

Also, in this production process, the group —A— is preferably a group represented by the formula,

wherein $R^2$ and the bond $\sim$ have the same meanings as defined above.

Not only can the cephalosporin represented by the formula [I] or a salt thereof thus obtained be isolated and purified in the conventional manner, but the compound represented by the formula [I] in which $R^{5a}$ is a carboxyl-protecting group can also be readily converted to the compound represented by the formula [I] in which $R^{5a}$ is a hydrogen atom or a salt thereof, in the conventional manner.

Further, this invention covers all the optical isomers, racemic compounds, and all crystal forms and hydrates of the compounds represented by the formula [I] or a salt thereof.

In the above formulas, X is a halogen atom, and $R^1$, $R^2$ and the bond $\sim$ have the same meanings as defined above.

(a) Preparation of thiolo esters represented by the formula [IV] and [IX]

According to the method described in Bulletin of The Chemical Society of Japan, 42, 1322–1324 (1969) or the like, a thiolo ester represented by the formula [IV] can be obtained from diketene.

This reaction is conducted in the presence or absence of a solvent in the presence of an acid-binding agent, for example, an inorganic base such as an alkali metal carbonate, an alkali metal hydrogencarbonate or the like; an organic base such as trialkylamine, pyridine, N,N-dimethylaminopyridine or the like; propylene oxide; or the like.

The reaction is usually carried out with cooling, at ambient temperatures or with heating, and completed in 1–10 hours.

And, the compound represented by the general formula [IX] can be obtained by reacting a thiol with a 4-halogeno-3-oxobutyryl halide represented by the formula [VIII] which is obtained by the reaction of diketene with a halogen such as chlorine, bromine or the like [Journal of The Chemical Society, 97, 1987 (1910)].

(b) Nitrosation

The nitroso compound represented by the formula [V] or [X] can be obtained by reacting a compound represented by the formula [IV] or [IX] with a nitrosating agent, respectively.

This reaction is usually conducted in a solvent. As the solvent, there may be used a solvent inert to the reaction such as water, acetic acid, benzene, methanol, ethanol, tetrahydrofuran or the like. The preferable examples of the nitrosating agent are nitrous acid or its derivatives, for example, nitrosyl halides such as nitrosyl chloride, nitrosyl bromide and the like; alkali metal nitrites such as sodium nitrite, potassium nitrite and the like; alkyl nitrites such as butyl nitrite, pentyl nitrite and the like; etc. When an alkali metal nitrite is used as the nitrosating agent, it is preferable to conduct the reaction in the presence of an inorganic or organic acid such as hydrochloric acid, sulfuric acid, formic acid, acetic acid or the like. When an alkyl nitrite is used as the nitrosating agent, it is preferable to conduct the reaction in the presence of a strong base such as an alkali metal alkoxide.

The reaction is usually carried out with cooling or at room temperature, and completed in 10 minutes to 10 hours.

(c) Etherification and phosphorylation

In order to obtain the compound represented by the formula [VI] or [VII] from the compound represented by the formula [V] or [X], respectively, the compound represented by the formula [V] or [X] is subjected to etherification or phosphorylation.

The etherification and the phosphorylation can be conducted according to the methods described in Japanese Patent Application Kokai (Laid-Open) Nos. 137,988/78, 105,689/80, 149,295/80 and the like.

And the alkylation, which is one of the typical examples of the etherification, is explained below in detail.

The alkylation can be conducted according to the conventional method. The reaction is usually carried out at a temperature of $-20°$ to $60°$ C., and completed in 5 minutes to 10 hours.

Any solvent may be used as far as it does not adversely affect the reaction, and there may be used, for example, diethyl ether, tetrahydrofuran, dioxane, methanol, ethanol, chloroform, methylene chloride, ethyl acetate, butyl acetate, N,N-dimethylformamide, N,N-dimethylacetamide, water or the like or a mixture thereof.

As the alkylating agent used for the reaction, there may be used, for example, lower alkyl halides such as methyl iodide, methyl bromide, ethyl iodide, ethyl bromide and the like; dimethyl sulfate; diethyl sulfate; diazomethane; diazoethane; tert.-butyl chloroacetate; methyl p-toluenesulfonate and the like. When the alkylating agents other than diazomethane and diazoethane are used, the reaction is usually carried out in the presence of a base, for example, an alkali metal carbonate such as sodium carbonate, potassium carbonate or the like; an alkali metal hydroxide such as sodium hydroxide, potassium hydroxide or the like; a trialkylamine; pyridine; N,N-dimethylaniline; or the like.

(d) Halogenation

The compound represented by the formula [VII] is obtained by reacting a halogenating agent with the compound represented by the formula [VI]. As the halogenating agent, there may be used, for example, a halogen such as bromine, chlorine or the like; a sulfuryl halide such as sulfuryl chloride or the like; a hypohalogenous acid or an alkali metal hypohalite such as hypochlorous acid, hypobromous acid, sodium hypochlorite or the like; an N-halogenated imide compound such as N-bromosuccinimide, N-chlorosuccinimide, N-bromophthalimide or the like; a perbromide compound such as pyridinium hydrobromideperbromide, 2-carboxyethyltriphenylphosphoniumperbromide or the like; etc.

This reaction is usually carried out in a solvent. As the solvent, there may be used a solvent which does not adversely affect the reaction, for example, a halogenated hydrocarbon such as methylene chloride, chloroform or the like; an organic carboxylic acid such as acetic acid, propionic acid or the like; an ether such as tetrahydrofuran, dioxane or the like; etc.

The reaction is usually carried out with cooling, at ambient temperatures or with heating, and completed in 30 minutes to 24 hours.

(e) Ring closure

The compound represented by the formula [IIa] or [IIb] is obtained by reacting thiourea with the compound represented by the formula [VII] or [IX], respectively. This reaction is usually carried out in a solvent. Any solvent may be used as far as it does not adversely affect the reaction, and includes, for example, water, methanol, ethanol, acetone, tetrahydrofuran, dioxane, N,N-dimethylformamide, N,N-dimethylacetamide, N-methylpyridone or the like, or a mixed solvent of two or more of them.

Although the addition of an acid-binding agent is not essential, the reaction sometimes proceeds smoothly upon addition of an acid-binding agent. As the acid-binding agent, there may be used an inorganic or organic base such as an alkali metal hydroxide, an alkali metal hydrogencarbonate, a trialkylamine, pyridine, N,N-dimethylaniline or the like.

Usually, thiourea is used in a proportion of 1 to several moles per mole of the compound represented by the formula [VII] or [IX]. The reaction is usually carried out at a temperature of $0°-100°$ C. The reaction time is usually 1-48 hours, preferably 1-10 hours.

The compounds obtained by the respective reactions mentioned above can be isolated or separated (in the case of isomers such as syn- and anti-isomers and the like) in the conventional manner, or alternatively, the reaction mixtures may be used for the subsequent reactions without isolation or separation.

Also, the compound represented by the formula [III] is obtained by, for example, subjecting a 7-amino cephalosporanic acid to a conventional conversion reaction at the 3-position in the presence of an acid [Japanese Patent Application Kokai (Laid-Open) Nos. 93,085/84, 98,089/84; and Japanese Patent Application Nos. 67,871/83, 113,565/83, 114,313/83 and the like], and then introducing a protecting group into the carboxyl group at the 4-position.

This invention is explained below referring to Referential Examples and Examples. However, this invention should not be interpreted to be limited to the Examples.

REFERENTIAL EXAMPLE 1

(1) To 330 ml of water were added 38.0 g of sodium nitrite and 66.1 g of 3-oxothiobutyric·acid-S-methyl ester, and 210 ml of 4N sulfuric acid was added dropwise to the resulting mixture with stirring at $5°-8°$ C. over a period of 30 minutes. After completion of the dropwise addition, the resulting mixture was subjected to reaction at the same temperature for 30 minutes, and the reaction mixture was introduced into 500 ml of ethyl acetate. The organic layer was separated, washed with 500 ml of water and dried over anhydrous magnesium sulfate, and the organic solvent was removed by distillation under reduced pressure. The residue obtained was dissolved in 650 ml of an aqueous solution containing 106 g of sodium carbonate, and then 150 ml of methanol was added to the resulting solution. To the resulting solution was added dropwise 75.7 g of dimethyl sulfate at 15°-20° C., and then the resulting mixture was subjected to reaction at the same temperature for 2 hours. Then, the reaction mixture was introduced into 1 liter of ethyl acetate, and thereafter the organic layer was separated, washed with 300 ml of water and then dried over anhydrous magnesium sulfate. The solvent was removed by distillation under reduced pressure, and the residue obtained was distilled under reduced pressure to obtain 60.4 g (yield, 68.9%) of 2-methoxyimino-3-oxothiobutyric acid-S-methyl ester (mixture of syn- and anti-isomers) having a boiling point of 80°-86° C./2 mmHg.

This mixture was separated and purified by a column chromatography (Wako Silica Gel C-200, eluant: n-hexane-benzene) to obtain 2-(syn)-methoxyimino-3-oxothiobutyric acid-S-methyl ester and 2-(anti)-methoxyimino-3-oxothiobutyric acid-S-methyl ester each in the form of an oily product.

2-(syn)-methoxyimino-3-oxothiobutyric acid-S-methyl ester

IR (neat)cm$^{-1}$: $\nu_{C=O}$ 1720, 1690, 1670

NMR (CDCl$_3$) δ value: 2.42(3H, s), 2.48(3H, s), 4.18(3H, s)

2-(anti)-methoxyimino-3-oxothiobutyric acid-S-methyl ester

IR (neat)cm$^{-1}$: $\nu_{C=O}$ 1750, 1680

NMR (CDCl$_3$) δ value: 2.41(3H, s), 2.42(3H, s), 4.16(3H, s)

(2) In 150 ml of 1,4-dioxane was dissolved 10.0 g of the 2-methoxyimino-3-oxothiobutyric acid-S-methyl ester (mixture of syn- and anti-isomers) obtained in above (1), and 20.1 g of pyridinium hydrobromide-perbromide was added to the solution, after which the resulting mixture was subjected to reaction at room temperature for 4 hours. Then, the solvent was removed by distillation under reduced pressure, and 100 ml of ethyl acetate and 100 ml of water were added to the residue obtained. The organic layer was separated, washed with 100 ml of 5% by weight aqueous sodium hydrogen sulfite solution, 100 ml of water and 100 ml of saturated aqueous sodium chloride solution in this sequence, and dried over anhydrous magnesium sulfate. The solvent was removed by distillation under reduced pressure to obtain 11.6 g (yield, 80.0%) of 4-bromo-2-methoxyimino-3-oxothiobutyric acid-S-methyl ester (mixture of syn- and anti-isomers).

The mixture was separated and purified by a column chromatography (Wako Silica Gel C-200, eluant: n-hexane-benzene) to obtain 4-bromo-2-(syn)-methoxyimino-3-oxothiobutyric acid-S-methyl ester and 4-bromo-2-(anti)-methoxyimino-3-oxothiobutyric acid-S-methyl ester each in the form of an oily product.

4-Bromo-2-(syn)-methoxyimino-3-oxothiobutyric acid-S-methyl ester

IR (neat)cm$^{-1}$: $\nu_{C=O}$ 1705, 1665

NMR (CDCl$_3$) δ value: 2.52(3H, s, —SCH$_3$), 4.21 (3H, s, —OCH$_3$), 4.42(2H, s, BrCH$_2$—)

4-Bromo-2-(anti)-methoxyimino-3-oxothiobutyric acid-S-methyl ester

IR (neat)cm$^{-1}$: $\nu_{C=O}$ 1720, 1655

NMR (CDCl$_3$) δ value: 2.41(3H, s, —SCH$_3$), 4.21 (3H, s, —OCH$_3$), 4.23(2H, s, BrCH$_2$—)

(3) In 50 ml of N,N-dimethylacetamide was dissolved 3.3 g of thiourea, and 10.0 g of the 4-bromo-2-methoxyimino-3-oxothiobutyric acid-S-methyl ester (mixture of syn- and anti-isomers) obtained in above (2) was added to the resulting solution while cooling with water, after which the resulting mixture was subjected to reaction at room temperature for 1 hour. Then, the reaction mixture was introduced into a mixed solvent of 150 ml of ethyl acetate and 100 ml of water, and the pH was adjusted to 7.0 with sodium hydrogencarbonate. The organic layer was separated, washed with 100 ml of water and 100 ml of saturated aqueous sodium chloride solution in this sequence, and then dried over anhydrous magnesium sulfate. The solvent was removed by distillation under reduced pressure, and the residue thus obtained was separated and purified by a column chromatography (Wako Silica Gel C-200, eluant: benzene-ethyl acetate) to obtain 4.6 g (yield, 50.5%) of 2-(2-aminothiazol-4-yl)-2-(syn)-methoxyiminothioacetic acid-S-methyl ester having a melting point of 178°-179° C. and 1.6 g (yield, 17.6%) of 2-(2-aminothiazol-4-yl)-2-(anti)-methoxyiminothioacetic acid-S-methyl ester having a melting point of >200° C.

2-(2-Aminothiazol-4-yl)-2-(syn)-methoxyiminothioacetic acid-S-methyl ester

IR (KBr)cm$^{-1}$: $\nu_{C=O}$ 1725, 1660

NMR (d$_6$-DMSO) δ value: 2.48 (3H, s, —SCH$_3$), 3.98(3H, s, —OCH$_3$), 7.07(1H, s,

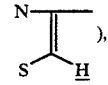

7.11(2H, bs, —NH$_2$)

2-(2-Aminothiazol-4-yl)-2-(anti)-methoxyiminothioacetic acid-S-methyl ester

IR (KBr)cm$^{-1}$: $\nu_{C=O}$ 1660

NMR (d$_6$-DMSO) δ value: 2.40(3H, s, —SCH$_3$), 4.25(3H, s, —OCH$_3$), 7.78(1H, s,

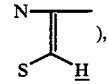

9.50(2H, bs, —NH$_2$)

REFERENTIAL EXAMPLE 2

(1) In 60 ml of acetic acid was dissolved 10.2 g of 3-oxothiobutyric acid-S-ethyl ester, and 5.8 g of sodium nitrite was added to the resulting solution over a period of 10 minutes while maintaining the temperature of the solution at 15°-20° C. After the resulting mixture was subjected to reaction at the same temperature for 50 minutes, the reaction mixture was introduced into a mixed solvent of 300 ml of ethyl acetate and 100 ml of water. The organic layer was separated, washed with 50 ml of saturated aqueous sodium chloride solution, and thereafter dried over anhydrous magnesium sulfate. The solvent was removed by distillation under reduced pressure. After the residue thus obtained was dissolved in 200 ml of an aqueous solution containing 14.8 g of sodium carbonate, 70 ml of methanol was added to the resulting solution. To this solution was added dropwise 9.7 g of dimethyl sulfate at a temperature of 5°-10° C., the resulting mixture was subjected to reaction at room temperature for 1 hour. Then, the reaction mixture was introduced into 150 ml of ethyl acetate, and the organic layer was separated, washed with 50 ml of water and 30 ml of saturated aqueous sodium chloride solution in this sequence and dried over anhydrous magnesium sulfate. The solvent was removed by distillation under reduced pressure, and the residue obtained was distilled under reduced pressure to obtain 7.0 g (yield, 53.0%) of 2-methoxyimino-3-oxothiobutyric acid-S-ethyl ester (mixture of syn- and anti-isomers) having a boiling point of 95°–100° C./1 mmHg.

This mixture was separated and purified by a column chromatography (Wako Silica Gel C-200, eluant: n-hexane-benzene) to obtain 2-(syn)-methoxyimino-3-oxothiobutyric acid-S-ethyl ester and 2-(anti)-methoxyimino-3-oxothiobutyric acid-S-ethyl ester each in the form of an oily product.

2-(syn)-methoxyimino-3-oxothiobutyric acid-S-ethyl ester

IR (neat)cm$^{-1}$: $\nu_{C=O}$ 1700, 1670

NMR (CDCl$_3$) δ value: 1.33(3H, t, J=7 Hz, —CH$_2$CH$_3$), 2.41(3H, s,

3.10(2H, q, J=7 Hz, —CH$_2$CH$_3$), 4.13(3H, s, —OCH$_3$)

2-(anti)-methoxyimino-3-oxothiobutyric acid-S-ethyl ester

IR (neat)cm$^{-1}$: $\nu_{C=O}$ 1730, 1675, 1660

NMR (CDCl$_3$) δ value: 1.29(3H, t, J=7 Hz, —CH$_2$CH$_3$), 2.36(3H, s,

2.99(2H, q, J=7 Hz, —CH$_2$CH$_3$), 4.11(3H, s, —OCH$_3$)

(2) 4-Bromo-2-methoxyimino-3-oxothiobutyric acid-S-ethyl ester (mixture of syn- and anti-isomers; yield, 76.5%) was obtained by repeating the same procedure as in Referential Example 1-(2) except that 2-methoxyimino-3-oxothiobutyric acid-S-ethyl ester (mixture of syn- and anti-isomers) was substituted for the 2-methoxyimino-3-oxothiobutyric acid-S-methyl ester. Then, the 4-bromo-2-methoxyimino-3-oxothiobutyric acid-S-ethyl ester (mixture of syn- and anti-isomers) was reacted with thiourea in the same manner as in Referential Example 1-(3) to obtain 2-(2-aminothiazol-4-yl)-2-methoxyiminoacetic acid-S-ethyl ester (syn-isomer; yield, 49.0%, anti-isomer; yield, 16.5%). Physical properties of the respective isomers separated are as shown below.

4-Bromo-2-(syn)-methoxyimino-3-oxothiobutyric acid-S-ethyl ester

Oily product

IR (neat)cm$^{-1}$: $\nu_{C=O}$ 1700, 1665 NMR (d$_6$-DMSO) δ value: 1.31(3H, t, J=7 Hz, —CH$_2$CH$_3$), 3.14(2H, q, J=7 Hz —CH$_2$CH$_3$), 4.20(3H, s, —OCH$_3$), 4.69(2H, s, BrCH$_2$—)

4-Bromo-2-(anti)-methoxyimino-3-oxothiobutyric acid-S-ethyl ester

Oily product

IR (neat)cm $^{-1}$: $\nu_{C=O}$ 1720, 1660

NMR (d$_6$-DMSO) δ value: 1.25(3H, t, J=7 Hz, —CH$_2$CH$_3$), 3.01(2H, q, J=7 Hz, —CH$_2$CH$_3$), 4.14(3H, s, —OCH$_3$), 4.59(2H, s, BrCH$_2$—)

2-(2-Aminothiazol-4-yl)-2-(syn)-methoxyiminothioacetic acid-S-ethyl ester

Melting point: 152°–153° C.

IR (KBr)cm$^{-1}$: $\nu_{C=O}$ 1725, 1655

NMR (d$_6$-DMSO) δ value: 1.29(3H, t, J=7 Hz, —CH$_2$CH$_3$), 3.12(2H, q, J=7 Hz, —CH$_2$CH$_3$), 3.95(3H, s, —OCH$_3$), 6.98(1H, s,

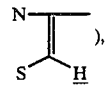

7.40(2H, bs, —NH$_2$)

2-(2-Aminothiazol-4-yl)-2-(anti)-methoxyiminothioacetic acid-S-ethyl ester

Melting point: 102°–103° C.

IR (KBr)cm$^{-1}$: $\nu_{C=O}$ 1660

NMR (d$_6$-DMSO) δ value: 1.25(3H, t, J=7 Hz, —CH$_2$CH$_3$), 3.00(2H, q, J=7 Hz, —CH$_2$CH$_3$), 4.10(3H, s, —OCH$_3$), 7.21(1H, s

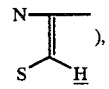

7.49(2H, bs, —NH$_2$)

REFERENTIAL EXAMPLE 3

(1) In 10 ml of acetic acid was dissolved 1.74 g of 3-oxothiobutyric acid-S-tert.-butyl ester, and 0.81 g of sodium nitrite was added to the resulting solution over a period of 10 minutes while maintaining the temperature of the mixture at 15°–20° C. After the resulting mixture was subjected to reaction at room temperature for 50 minutes, the reaction mixture was introduced into a mixed solvent of 50 ml of ethyl acetate and 30 ml of water. The organic layer was separated, washed with 20 ml of saturated aqueous sodium chloride solution, and dried over anhydrous magnesium sulfate, and the solvent was removed by distillation under reduced pressure. To the residue obtained was added 13 ml of 6.8% by weight solution of diazomethane in diethyl ether, and the resulting mixture was subjected to reaction at room temperature for 1 hour. Then, the reaction mixture was concentrated under reduced pressure, and the residue obtained was purified by a column chromatography (Wako Silica Gel C-200, eluant: n-hexane-ethyl acetate) to obtain 1.08 g (yield, 49.7%) of 2-(syn)-methoxyimino-3-oxothiobutyric acid-S-tert.-butyl ester in the form of an oily product.

IR (neat)cm$^{31\ 1}$: $\nu_{C=O}$ 1695, 1665, 1580

NMR (CDCl$_3$) δ value: 1.59(9H, s, —C(CH$_3$)$_3$), 2.40(3H, s,

4.15(3H, s, CH$_3$O—)

(2) The bromo compound (mixture of syn- and anti-isomers; yield, 82.0%) was obtained by reacting the 2-(syn)-methoxyimino-3-oxothiobutyric acid-S-tert.-butyl ester obtained in above (1) in the same manner as in Referential Example 1-(2). Then, the 4-bromo-2- methoxyimino-3-oxothiobutyric acid-S-tert.-butyl ester (mixture of syn- and anti-isomers) thus obtained was reacted with thiourea in the same manner as in Referential Example 1-(3) to obtain 2-(2-amino-thiazol-4-yl)-2-methoxyiminothioacetic acid-S-tert.-butyl ester (syn-isomer; yield, 54.2%, anti-isomer; yield, 20.3%). Physical properties of the respective isomers separated are as shown below.

4-Bromo-2-(syn)-methoxyimino-3-oxothiobutyric acid-S-tert.-butyl ester
Oily product
IR (neat)cm$^{-1}$: $\nu_{C=O}$ 1705, 1660
NMR (CDCl$_3$) δ value: 1.58(9H, s, —C(CH$_3$)$_3$), 4.21(3H, s, —OCH$_3$), 4.42(2H, s, BrCH$_2$—)

4-Bromo-2-(anti)-methoxyimino-3-oxothiobutyric acid-S-tert.-butyl ester
Oily product
IR (neat)cm$^{-1}$: $\nu_{C=O}$ 1730, 1655
NMR (CDCl$_3$) δvalue: 1.54(9H, s, —C(CH$_3$)$_3$), 4.18(3H, s, —OCH$_3$), 4.22(2H, s, BrCH$_2$—)

2-(2-Aminothiazol-4-yl)-2-(syn)-methoxyiminothioacetic acid-S-tert.-butyl ester
IR (KBr)cm$^{-1}$: $\nu_{C=O}$ 1660
NMR (CDCl$_3$) δ value: 1.60(9H, s, —C(CH$_3$)$_3$), 4.01(3H, s, —OCH$_3$), 6.12(2H, bs, —NH$_2$), 6.72(1H, s,

)

2-(2-Aminothiazol-4-yl)-2-(anti)-methoxyiminothioacetic acid-S-tert.-butyl ester
IR (neat)cm$^{-1}$: $\nu_{C=O}$ 1725, 1660
NMR (CDCl$_3$) δ value: 1.53(9H, s, —C(CH$_3$)$_3$), 4.12(3H, s, —OCH$_3$), 5.85(2H, bs, —NH$_2$), 7.35(1H, s,

)

REFERENTIAL EXAMPLE 4

(1) In 40 ml of anhydrous methylene chloride was dissolved 8.4 g of diketene, and the resulting solution was cooled to −40° C. Then, 14.4 g of bromine was added dropwise to the solution while maintaining the temperature at −40° to −35° C. over a period of 1 hour, and the resulting mixture was subjected to reaction at −30° to −20° C. for 30 minutes. On the other hand, 7.48 g of ethanethiol and 5.84 g of propylene oxide were dissolved in 60 ml of anhydrous methylene chloride, and the resulting solution was cooled to −40° C. Into this solution was introduced the above-mentioned reaction mixture. Then, the temperature of the reaction mixture was raised up to room temperature over a period of 1 hour, and the mixture was further subjected to reaction at the same temperature for 1 hour. The reaction mixture was introduced into 100 ml of water at 5° C., and the pH was adjusted to 6.0 with sodium hydrogencarbonate. The organic layer was separated, washed with 30 ml of saturated aqueous sodium chloride solution and then dried over anhydrous magnesium sulfate. The solvent was removed by distillation under reduced pressure and the residue obtained was distilled under reduced pressure to obtain 11.8 g (yield, 58.0%) of 4-bromo-3-oxothiobutyric acid-S-ethyl ester having a boiling point of 110°–120° C./4 mmHg.
IR (neat)cm$^{-1}$: $\nu_{C=O}$ 1725, 1675, 1625
NMR (CDCl$_3$) δ value: 1.33(3H, t, J=7 Hz, —CH$_2$CH$_3$), 3.05(2H, q, J=7 Hz, —CH$_2$CH$_3$), 3.95(2H×⅓, s, BrCH$_2$—), 4.04(2H×⅔, s, —COCH$_2$CO—), 4.21(2H×⅔, s, BrCH$_2$—), 5.83(1H×⅓, s, <C=CH—)
(In this compound, the above expression was used, because the keto type and the enol type were present in a ratio nearly equal to (2:1).)

(2) In 6 ml of acetic acid was dissolved 1.13 g of the 4-bromo-3-oxothiobutyric acid-S-ethyl ester obtained in above (1), and 0.41 g of sodium nitrite was added to the resulting solution over a period of 10 minutes while maintaining the temperature at 15°–20° C. Then, the resulting mixture was subjected to reaction at room temperature for 50 minutes, and then the reaction mixture was introduced into a mixed solvent of 30 ml of ethyl acetate and 20 ml of water. The organic layer was separated, washed with 10 ml of saturated aqueous sodium chloride solution and dried over anhydrous magnesium sulfate. The solvent was removed by distillation under reduced pressure, and the residue obtained was dissolved in 10 ml of diethyl ether, whereafter 6 ml of 6.8% by weight solution of diazomethane in diethyl ether was added to the resulting solution, and the resulting mixture was subjected to reaction at room temperature for 1 hour. Then, the reaction mixture was concentrated under reduced pressure, and the residue obtained was purified by a column chromatography (Wako Silica Gel C-200, eluant: n-hexane-ethyl acetate) to obtain 0.53 g (yield, 39.0%) of 4-bromo-2-(syn)-methoxyimino-3-oxothiobutyric acid-S-ethyl ester in the form of an oily product. The physical properties (IR, NMR) of this compound were identical with those of the compound obtained in Referential Example 2-(2).

(3) 2-(2-Aminothiazol-4-yl)-2-(syn)-methoxyiminothioacetic acid-S-ethyl ester was obtained by reacting the 4-bromo-2-(syn)-methoxyimino-3-oxothiobutyric acid-S-ethyl ester in the same manner as in Referential Example 1-(3). The physical properties (melting point, IR, NMR) of this compound were identical with those of the compound obtained in Referential Example 2-(2).

(4) Furthermore, the following compound was obtained by conducting reaction in the same manner as in above (1), (2) and (3):
2-(2-Aminothiazol-4-yl)-2-(syn)-methoxyiminothioacetic acid-S-phenyl ester
Melting point: 130°–134° C.
IR (KBr)cm$^{-1}$: $\nu_{C=O}$ 1670, 1605
NMR (d$_6$-DMSO) δ value: 3.93(3H, s, —OCH$_3$), 6.97(1H, s,

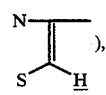
), 7.41(2H, bs, —NH$_2$), 7.58(5H, s,

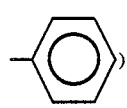
)

REFERENTIAL EXAMPLE 5

(1) In 10 ml of N,N-dimethylformamide was dissolved 1.75 g of 2-hydroxyimino-3-oxothiobutyric acid-S-ethyl ester, and 1.38 g of potassium carbonate was added to the resulting solution. Then, 1.81 g of tert.-butyl chloroacetate was added to the resulting mixture with ice-cooling, and the mixture was subjected to reaction at room temperature for 2 hours. The reaction mixture was introduced into a mixed solvent of 30 ml of ethyl acetate and 30 ml of water. The organic layer was separated, washed with two 30-ml portions of water and with 20 ml of saturated aqueous sodium chloride solution, and dried over anhydrous magnesium sulfate. Then, the solvent was removed by distillation under reduced pressure, and the residue obtained was purified by a column chromatography (Wako Silica Gel C-200, eluant: n-hexane-benzene) to obtain 2.11 g (yield, 72.9%) of 2-(syn)-tert.-butoxycarbonylmethoxyimino-3-oxothiobutyric acid-S-ethyl ester in the form of an oily product.

IR (neat)cm$^{-1}$: $\nu_{C=O}$ 1750, 1660, 1600

NMR (CDCl$_3$) δ value: 1.34(3H, t, J=7 Hz, —CH$_2$CH$_3$), 1.50(9H, s, —C(CH$_3$)$_3$), 2.39(3H, s, CH$_3$CO—), 3.12(2H, q, J=7 Hz, —CH$_2$CH$_3$), 4.69(2H, s, —OCH$_2$CO—)

(2) In 45 ml of 1,4-dioxane was dissolved 2.89 g of 2-(syn)-tert.-butoxycarbonylmethoxyimino-3-oxothiobutyric acid-S-ethyl ester, and 3.20 g of pyridinium hydrobromide-perbromide was added to the resulting solution, after which the resulting mixture was subjected to reaction at room temperature for 4 hours. The solvent was removed by distillation under reduced pressure, and 50 ml of ethyl acetate and 50 ml of water were added to the residue obtained. Then, the organic layer was separated, washed with 50 ml of 5% by weight aqueous sodium hydrogen sulfite solution, 50 ml of water and 50 ml of saturated aqueous sodium chloride solution in this sequence, and dried over anhydrous magnesium sulfate. The solvent was removed by distillation under reduced pressure, and the residue obtained was purified by a column chromatography (Wako Silica Gel C-200, eluant: n-hexane-benzene) to obtain 2.05 g (yield, 55.8%) of 4-bromo-2-(syn)-tert.-butoxycarbonylmethoxyimino-3-oxothiobutyric acid-S-ethyl ester in the form of an oily product.

IR (neat)cm$^{-1}$: $\nu_{C=O}$ 1730, 1660

NMR (CDCl$_3$) δ value: 1.42(3H, t, J=7 Hz, —CH$_2$CH$_3$), 1.58(9H, s, —C(CH$_3$)3), 3.21(2H, q, J=7 Hz, —CH$_2$CH$_3$), 4.43(2H, s, BrCH$_2$—), 4.99(2H, s, —OCH$_2$CO—)

(3) In 15 ml of N,N-dimethylacetamide was dissolved 3.68 g of 4-bromo-2-(syn)-tert.-butoxycarbonylmethoxyimino-3-oxothiobutyric acid-S-ethyl ester, and 0.84 g of thiourea was added to the resulting solution with ice-cooling, after which the resulting mixture was subjected to reaction at room temperature for 1 hour. The reaction mixture was introduced into a mixed solvent of 50 ml of ethyl acetate and 50 ml of water, and the pH was adjusted to 5.0 with sodium hydrogencarbonate. Then, the organic layer was separated, washed with two 50-ml portions of water and with 30 ml of saturated aqueous sodium chloride solution, and dried over anhydrous magnesium sulfate. The solvent was removed by distillation under reduced pressure, and diethyl ether was added to the residue thus obtained. The resulting mixture was filtered to obtain 1.10 g (yield, 31.8%) of 2-(2-aminothiazol-4-yl)-2-(syn)-tert.-butoxycarbonylmethoxyiminothioacetic acid-S-ethyl ester having a melting point of 168°–169° C. The filtrate was concentrated under reduced pressure, and the residue obtained was purified by a column chromatography (Wako Silica Gel C-200, eluant: benzene-ethyl acetate) to obtain 0.44 g (yield, 12.8%) of 2-(2-aminothiazol-4-yl)-2-(anti)-tert.-butoxycarbonylmethoxyiminothioacetic acid-S-ethyl ester having a melting point of 78°–79° C.

2-(2-Aminothiazol-4-yl)-2-(syn)-tert.-butoxycarbonylmethoxyiminothioacetic acid-S-ethyl ester IR (KBr)cm$^{-1}$: $\nu_{C=O}$ 1720, 1660

NMR (CDCl$_3$) δ value: 1.38(3H, t, J=7 Hz, —CH$_2$CH$_3$), 1.53(9H, s, —C(CH$_3$)$_3$), 3.17(2H, q, J=7 Hz, —CH$_2$CH$_3$), 4.66(2H, s, —OCH$_2$CO—), 6.58(2H, bs, H$_2$N—), 6.76(1H, s,

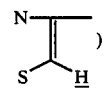
)

2-(2-Aminothiazol-4-yl)-2-(anti)-tert.-butoxycarbonylmethoxyiminothioacetic acid-S-ethyl ester IR (KBr)cm$^{-1}$: $\nu_{C=O}$ 1740, 1670

NMR (CDCl$_3$) δ value: 1.30(3H, t, J=7 Hz, —CH$_2$CH$_3$), 1.51(9H, s, —C(CH$_3$)$_3$), 2.99(2H, q, J=7 Hz, —CH$_2$CH$_3$), 4.72(2H, s, —OCH$_2$CO—), 6.00(2H, bs, H$_2$N—), 7.50(1H, s,

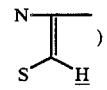
)

REFERENTIAL EXAMPLE 6

In 7.0 ml of N,N-dimethylacetamide was dissolved 2.25 g of the 4-bromo-3-oxothiobutyric acid-S-ethyl ester obtained in Referential Example 4-(1), and 1.14 g of thiourea was added to the resulting solution with ice-cooling, after which the resulting mixture was subjected to reaction at room temperature for 1 hour. The reaction mixture was introduced into a mixed solvent of 50 ml of ethyl acetate and 50 ml of water, and the pH was adjusted to 6.0 with sodium hydrogencarbonate. Then, the organic layer was separated, washed with two 50-ml portions of water and with 50 ml of saturated aqueous sodium chloride solution, and dried over anhydrous magnesium sulfate. Then the solvent was removed by distillation under reduced pressure. The residue obtained was recrystallized from 20 ml of ethyl acetate to obtain 1.32 g (yield, 65.5%) of 2-(2-aminothiazol-4-yl)thioacetic acid-S-ethyl ester having a melting point of 76°–77° C.

IR (KBr)cm$^{-1}$: $\nu_{C=O}$ 1655

NMR (CDCl$_3$) δ value: 1.22(3H, t, J=7 Hz, —CH$_2$CH$_3$), 2.89(2H, q, J=7 Hz, —CH$_2$CH$_3$), 3.74(2H, bs,

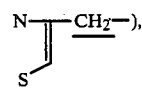
, 5.76(2H, bs, H$_2$N—), 6.29(1H, s,

EXAMPLE 1

In 50 ml of anhydrous methylene chloride was suspended 6.94 g of 2-(2-aminothiazol-4-yl)-2-(syn)-methoxyiminothioacetic acid-S-methyl ester, and 4.26 g of boron trifluoride-diethyl ether complex was added with ice-cooling to the resulting suspension to form a solution. Then, 40 ml of an anhydrous methylene chloride solution containing 4.10 g of pivaloyloxymethyl 7-amino-3-[2-(5-methyl-1,2,3,4-tetrazolyl)]methyl-$\Delta^3$-cephem-4-carboxylate was added to the solution, and the resulting mixture was subjected to reaction at room temperature for 7 hours. The reaction mixture obtained was introduced into 50 ml of water, and the organic layer was separated. Then, 50 ml of water was added to the organic layer, and the pH was adjusted to 0.5 with 6N hydrochloric acid. Then, the organic layer was separated, and 50 ml of water was added thereto. The pH was adjusted to 5.0 with sodium hydrogencarbonate. The organic layer was further separated, washed with 50 ml of saturated aqueous sodium chloride solution, and then dried over anhydrous magnesium sulfate. After removing the solvent by distillation under reduced pressure, the residue obtained was dissolved in 80 ml of ethyl acetate. Then, 2.36 g of mesitylenesulfonic acid dihydrate was added to the resulting solution, and stirred for 30 minutes, and the precipitated crystals were collected by filtration to obtain 7.05 g (yield, 88.8%) of mesitylenesulfonic acid salt of pivaloyloxymethyl 7-[2-(2-aminothiazol-4-yl)-2-(syn)-methoxyiminoacetamido]-3-[2-(5-methyl-1,2,3,4-tetrazolyl)-]methyl-$\Delta^3$-cephem-4-carboxylate having a melting point of 218°-220° C. (decomp.).

IR (KBr)cm$^{-1}$: $\nu_{C=O}$ 1782, 1745, 1680

NMR (d$_6$-DMSO) δ value: 1.15(9H, s, —C(CH$_3$)$_3$), 2.14(3H, s,

2.43(3H, s,

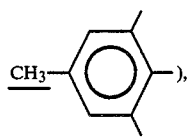

2.53(6H, s,

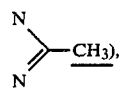

3.52(2H, bs, C$_2$—H), 3.93(3H, s, —OCH$_3$), 5.20(1H, d, J=5 Hz, C$_6$—H), 5.56(2H, bs,

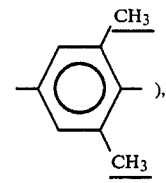

5.78(1H, dd, J=5 Hz, J=8 Hz, C$_7$—H), 5.85(2H, s, —OCH$_2$O—), 6.75(2H, s,

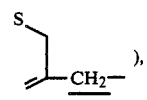

6.94(1H, s,

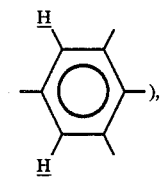

When reactions were carried out in the same manner as above under the reaction conditions shown in Table 1, mesitylenesulfonic acid salt of pivaloyloxymethyl 7-[2-(2-aminothiazol-4-yl)-2-(syn)-methoxyiminoacetamido]-3-[2-(5-methyl-1,2,3,4-tetrazolyl)-]methyl-$\Delta^3$-cephem-4-carboxylate was obtained. The physical properties (melting point, IR, NMR) of the product were identical with those of the compound obtained above.

TABLE 1

| Run No. | 2-(2-Aminothiazol-4-yl)-2-(syn)-methoxyimino-thioacetic acid-S-methyl ester (g) | Pivaloyloxymethyl 7-amino-3-[2-(5-methyl-1,2,3,4-tetrazolyl)]-methyl-$\Delta^3$-cephem-4-carboxylate (g) | BF$_3$—Et$_2$O (g) | Solvent | Reaction Temperature Reaction Time (hour) | Yield (g)/ yield (%) |
|---|---|---|---|---|---|---|
| 1 | 2.54 | 4.10 | 2.27 | CH$_2$Cl$_2$ | Room temp. 8 | 4.76/60 |
| 2 | 5.09 | 4.10 | 3.12 | CH$_2$Cl$_2$ | Room temp. 8 | 6.43/81 |
| 3 | 6.94 | 4.10 | 4.26 | ClCH$_2$CH$_2$Cl | Room temp. 8 | 6.75/85 |

The same reaction as above was carried out, except that one of the following starting materials was substituted for the 2-(2-aminothiazol-4-yl)-2-(syn)-methoxyiminothioacetic acid-S-methyl ester to obtain the mesitylenesulfonic acid salt of pivaloyloxymethyl 7-[2-(2- aminothiazol-4-yl)-2-(syn)-methoxyiminoacetamido]-3-[-2-(5-methyl-1,2,3,4-tetrazolyl)]methyl-Δ³-cephem-4-carboxylate. The physical properties (melting point, IR, NMR) of the product obtained were identical with those of the compound obtained above.

TABLE 2

| No. | Starting material | Yield (%) |
|---|---|---|
| 1 | 2-(2-Aminothiazol-4-yl)-2-(syn)-methoxyiminothioacetic acid-S—ethyl ester | 85.0 |
| 2 | 2-(2-Aminothiazol-4-yl)-2-(syn)-methoxyiminothioacetic acid-S—phenyl ester | 75.2 |

EXAMPLE 2

(1) In 10 ml of anhydrous methylene chloride was suspended 1.39 g of 2-(2-aminothiazol-4-yl)-2-(syn)-methoxyiminothioacetic acid-S-methyl ester, and 0.85 g of boron trifluoride-diethyl ether complex was added with ice-cooling to the resulting suspension to form a solution. Then, 10 ml of an anhydrous methylene chloride solution containing 0.76 g of diphenylmethyl 7-amino-3-methyl-Δ³-cephem-4-carboxylate was added to the solution, and the resulting mixture was subjected to reaction at room temperature for 4 hours. The reaction mixture obtained was introduced into 20 ml of water, and the organic layer was thereafter separated, after which 20 ml of water was added thereto. Then, the pH was adjusted to 0.5 with 6N hydrochloric acid. Then, the organic layer was separated, and 20 ml of water was added thereto, after which the pH was adjusted to 5.0 with sodium hydrogencarbonate. Moreover, the organic layer was separated, washed with 10 ml of saturated aqueous sodium chloride solution, and then dried over anhydrous magnesium sulfate. The solvent was removed by distillation under reduced pressure, and the residue obtained was purified by a column chromatography (Wako Silica Gel C-200, eluant: chloroformmethanol) to obtain 0.95 g (yield, 84.0%) of diphenylmethyl 7-[2-(2-aminothiazol-4-yl)-2-(syn)-methoxyiminoacetamido]-3-methyl-Δ³-cephem-4-carboxylate having a melting point of 104°-106° C. (decomp.).

IR (KBr) cm⁻¹: $\nu_{C=O}$ 1770, 1720, 1670, 1610
NMR (CDCl₃) δ value: 2.10(3H, s, —CH₃), 3.35(2H, bs, C₂—H), 4.06(3H, s, —OCH₃), 5.11(1H, d, J=5 Hz, C₆—H), 6.04(1H, dd, J=5 Hz, J=8 Hz, C₇—H), 6.78(1H, s,

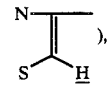), 7.03(1H, s, —CH<), 7.19–7.78 (10H, m,

), 8.40 (1H, d, J=8 Hz, —CONH—)

When the same reaction as above was carried out, except that one of the starting compounds shown in Table 3 was substituted for the diphenylmethyl 7-amino-3-methyl-Δ₃-cephem 4-carboxylate, to obtain the objective compounds shown in Table 3.

TABLE 3

| Run No. | Starting compound | Objective compound Yield (%) | No.* |
|---|---|---|---|
| 1 | Diphenylmethyl 7-amino-3-[1-(5-chloro-1,2,4-triazolyl)]methyl-Δ³-cephem-4-carboxylate | 86.0 | A |
| 2 | Diphenylmethyl 7-amino-3-[1-(4-ethyl-2,3-dioxo-1,2,3,4-tetrahydropyrazinyl)]methyl-Δ³-cephem-4-carboxylate | 84.0 | B |
| 3 | Diphenylmethyl 7-amino-3-acetoxymethyl-Δ³-cephem-4-carboxylate | 72.5 | C |
| 4 | Diphenylmethyl 7-amino-3-[5-(1-methyl-1,2,3,4-tetrazolyl)]thiomethyl-Δ³-cephem-4-carboxylate | 71.3 | D |
| 5 | Diphenylmethyl 7-amino-3-[2-(5-methyl-1,2,3,4-**tetrazolyl)]methyl-Δ³-cephem-4-carboxylate | 70.5 | E |

Note:
*Physical properties are shown in Table 5.
**The reaction was carried out using 1 mole of boron trifluoride per mole of the thiolo ester compound in place of boron trifluoride-diethyl ether complex.

The same reaction as above was carried out, except that one of the starting compounds shown in Table 4 was substituted for the 2-(2-aminothiazol-4-yl)-2-(syn)-methoxyiminothioacetic acid-S-methyl ester and the diphenylmethyl 7-amino-3-methyl-Δ³-cephem-4-carboxylate, to obtain the objective compounds shown in Table 4.

TABLE 4

| Run No. | Starting compound | | Reaction time (hour) | Objective compound Yield (%) | No.* |
|---|---|---|---|---|---|
| 1 | 2-(2-Aminothiazol-4-yl)-2-(anti)-methoxyiminothioacetic acid-S—ethyl ester | Pivaloyloxymethyl 7-amino-3-[2-(5-methyl-1,2,3,4-tetrazolyl)]-methyl-Δ³-cephem-4-carboxylate | 16 | 75 | F |
| 2 | 2-(2-Aminothiazol-4-yl)-2-(syn)-tert.-butoxycarbonylmethoxyiminothioacetic acid-S—ethyl ester | Pivaloyloxymethyl 7-amino-3-[2-(5-methyl-1,2,3,4-tetrazolyl)]-methyl-Δ³-cephem-4-carboxylate | 7 | 55.4 | G |
| 3 | 2-(2-Aminothiazol-4-yl)-thioacetic acid S—ethyl ester | Pivaloyloxymethyl 7-amino-3-[2-(5-methyl-1,2,3,4-tetrazolyl)]- | 24 | 40 | H |

TABLE 4-continued

| Run No. | Starting compound | Reaction time (hour) | Objective compound Yield (%) | No.* |
|---|---|---|---|---|
| | methyl-$\Delta^3$-cephem-4-carboxylate | | | |

Note:
*Physical properties are shown in Table 5.

TABLE 5

Objective compound:

$$\text{H}_2\text{N}\underset{S}{\overset{N}{\diagdown}}\text{—A—CONH—}[\beta\text{-lactam}]\text{—CH}_2\text{—S—C(R}^6\text{)=CH—COOR}^{5a}$$

| No. | R⁵ᵃ | —A— | R⁶ | Melting point (°C.) | IR(KBr) cm⁻¹: νC=O | NMR(d₆-DMSO) δ value: |
|---|---|---|---|---|---|---|
| A | —CH(C₆H₅)₂ | $-\underset{\underset{OCH_3}{\parallel}}{C}-$ syn | 2-chloro-imidazol-... (—CH₂N, N=CH, Cl) | 155–157 (decomp.) | 1781, 1725, 1672 | 3.20 (2H,bs,C₂—H), 3.86 (3H,s,—OCH₃), 4.99 (1H,d,J = 5Hz,C₆—H), 4.82, 5.41 (2H,ABq,J = 16Hz, —CH₂—), 5.96 (1H,d,J = 5Hz,C₇—H), 6.62 (1H,s, N=C(S)—CH<), 6.92 (1H,s,—CH<), 7.28 (10H, C₆H₅ × 2), 7.71 (1H,s, N=CH—N) |
| B | —CH(C₆H₅)₂ | $-\underset{\underset{OCH_3}{\parallel}}{C}-$ syn | 1-ethyl-4-aminomethyl-2,3-dioxo-... (—CH₂N, N—C₂H₅) | 165–167 (decomp.) | 1780, 1720, 1680, 1640 | (measured in CDCl₃—D₂O) 1.18 (3H,t,J = 7Hz,—CH₂CH₃), 3.55 (2H,bs,C₂—H), 3.75 (2H,q, J = 7Hz,—CH₂CH₃), 3.90 (3H,s,—OCH₃), 4.41, 5.02(2H,ABq,J = 15Hz, —CH₂—), 5.26 (1H,d,J = 5Hz,C₆—H), 6.01 (1H,dd,J = 5Hz,J = 8Hz,C₇—H), 6.52, 6.65 (2H, ABq,J = 6Hz, >C=CH—), 6.88 (1H,s, N=C(S)—H), 7.07 (1H,s,—CH<), 7.15–7.84 |

TABLE 5-continued

Objective compound:

$$\text{H}_2\text{N} \underset{S}{\overset{N}{\diagdown}} \text{-A-CONH} \underset{O}{\overset{S}{\diagdown}} \underset{\text{COOR}^{5a}}{\overset{R^6}{\diagdown}}$$

| No. | —A— | R$^{5a}$ | R$^6$ | Melting point (°C.) | IR(KBr) cm$^{-1}$: νC=O | NMR(d$_6$-DMSO) δ value: |
|---|---|---|---|---|---|---|
| C | $-\underset{\underset{\text{OCH}_3}{\|\|}}{\overset{\|}{C}}=N}-$ syn | $-CH\underset{2}{\bigcirc}$ | —CH$_2$OCOCH$_3$ | 128–130 (decomp.) | 1780, 1730, 1670 | (10H,m, $\bigcirc \times 2$), 9.81 (1H,d, J = 8Hz, —CONH—) |
| | | | | | | 2.02 (3H,s,—COCH$_3$), 3.69 (2H,bs, C$_2$—H), 3.95 (3H,s,—OCH$_3$), 4.75, 5.06 (2H,ABq,J = 15Hz, —CH$_2$—), 5.37 (1H,d,J = 5Hz,C$_6$—H), 6.07 (1H, dd,J = 5Hz,J = 8Hz,C$_7$—H), 6.94(1H,s, $\underset{S}{\overset{N}{\diagdown}}\underset{\underset{H}{\|}}{C}-CH$), 7.11 (1H,s,—CH$\overset{\|}{}$), 7.26–7.84 (10H,m, $\bigcirc \times 2$), 9.93 (1H,d,J = 8Hz, —CONH—) |
| D | $-\underset{\underset{\text{OCH}_3}{\|\|}}{\overset{\|}{C}}=N}-$ syn | $-CH\underset{2}{\bigcirc}$ | $-CH_2S\underset{\underset{CH_3}{\|}}{\overset{N\text{---}N}{\diagup\diagdown}}\underset{N}{\overset{\|\|}{N}}$ | 115–117 (decomp.) | 1780, 1720, 1670 | 3.84 (2H,bs,C$_2$—H), 3.93 (6H,s, N—CH$_3$,—OCH$_3$), 4.37 (2H,bs, —CH$_2$—), 5.32 (1H,d,J = 5Hz,C$_6$—H), 6.03 (1H,dd,J = 5Hz,J = 8Hz,C$_7$—H), 6.89 (1H,s, $\underset{S}{\overset{N}{\diagdown}}\underset{\underset{H}{\|}}{C}$), 7.03 (1H,s, |

TABLE 5-continued

Objective compound:

$$\text{H}_2\text{N}\underset{S}{\overset{N}{\diagup}}\diagdown\text{A}-\text{CONH}\diagdown\text{...}\overset{S}{\underset{O}{\diagdown}}\diagdown\overset{R^6}{\underset{N}{\diagdown}}\diagdown\text{COOR}^{5a}$$

| No. | —A— | $R^{5a}$ | $R^6$ | Melting point (°C.) | IR(KBr) cm$^{-1}$; νC=O | NMR(d$_6$-DMSO) δ value: |
|---|---|---|---|---|---|---|
| E | $-\underset{\underset{OCH_3}{\parallel}}{C}=N$ syn | $-CH(\text{C}_6\text{H}_5)_2$ | $-CH_2-N\underset{N=N}{\overset{N}{\diagdown}}\diagup\overset{CH_3}{\diagdown}$ | 102-105 (decomp.) | 1778, 1720, 1660 | —CH(C$_6$H$_5$)$_2$, 7.16-7.80 (10H,m,—CONH—× 2), 9.82 (1H,d,J = 8Hz,—CONH—) 2.43 (3H,s,—CH$_3$), 3.45 (2H,bs, C$_2$—H), 3.84 (3H,s,—OCH$_3$), 5.29 (1H,d,J = 5Hz,C$_6$—H), 5.52 (2H, bs,—CH$_2$—), 5.93 (1H,dd,J = 5Hz, J = 8Hz,C$_7$—H), 6.78 (1H,s, thiazole-H), 6.91 (1H,s,—CH), 7.32 (10H, bs, —C$_6$H$_5$ × 2), 9.64 (1H,d,J = 8Hz,—CONH—) |
| F | $-\underset{\underset{OCH_3}{\parallel}}{C}=N$ antis | —CH$_2$OCOC-(CH$_3$)$_3$ | $-CH_2-N\underset{N=N}{\overset{N}{\diagdown}}\diagup\overset{CH_3}{\diagdown}$ | — | 1780, 1745, 1675 | — |

TABLE 5-continued

Objective compound:

$$\text{H}_2\text{N}\underset{\text{S}}{\overset{\text{N}}{\bigvee}}-\text{A}-\text{CONH}-\underset{\text{O}}{\overset{}{\underset{}{\bigsqcup}}}\underset{\text{N}}{\overset{\text{S}}{\bigvee}}\underset{\text{COOR}^{5a}}{\overset{\text{R}^6}{\bigvee}}$$

| No. | —A— | R$^{5a}$ | R$^6$ | Melting point (°C.) | IR(KBr) cm$^{-1}$: νC=O | NMR(d$_6$-DMSO) δ value: |
|---|---|---|---|---|---|---|
| G | $-\text{C}=\text{N}-\text{OCH}_2\text{COOC(CH}_3)_3$ syn | —CH$_2$OCOC(CH$_3$)$_3$ | —CH$_2$N(triazole)—CH$_3$ (N=N) | 95-97 (decomp.) | 1785, 1750, 1680 | 1.21 (9H,s,—C(CH$_3$)$_3$), 1.48 (9H,s, —C(CH$_3$)$_3$), 2.53 (3H,s, —CH$_3$ on triazole N), 3.59 (2H,bs,C$_2$—H), 4.66 (2H,s, —OCH$_2$CO—), 5.25 (2H,s, =CH$_2$—S), 5.37 (1H,d,J = 5Hz,C$_6$—H), 5.87-6.19 (3H,m,C$_7$—H, —OCH$_2$O—), 6.93 (1H,s, N=CH-S), 7.36(2H,bs,—NH$_2$), 9.77(1H,d,J = 8Hz,—CONH—) |
| H* | —CH$_2$— | —CH$_2$OCOC(CH$_3$)$_3$ | —CH$_2$N(triazole)—CH$_3$ (N=N) | 146-148 (decomp.) | 1782, 1750, 1670 | 1.15 (9H,s,—C(CH$_3$)$_3$), 2.46 (3H,s, —CH$_3$), 3.51 (2H,s,C$_2$—H), 3.62(2H,s, N=CH$_2$—S), 5.15(1H,d, J = 5Hz,C$_6$—H), 5.26-5.79 (3H,m, CH$_2$,C$_7$—H), 5.87(2H,s, —OCH$_2$O—), 6.62 (1H,s, N=CH-S), 9.23 (1H,d,J = 8Hz,—CONH—) |

*Hydrochloride (the hydrochloride was obtained in a conventional manner.)

(2) In a mixed solvent of 35 ml of trifluoroacetic acid and 10 ml of anisole was dissolved 6.65 g of di-phenylmethyl 7-[2-(2-aminothiazol-4-yl)-2-(syn)-methoxyiminoacetamido]-3-[1-(5-chloro-1,2,4-triazolyl)]-methyl-Δ³-cephem-4-carboxylate, and the resulting solution was subjected to reaction at room temperature for 1 hour. Then, the solvent was removed by distillation under reduced pressure, and diethyl ether was added to the residue, after which the crystals obtained were collected by filtration. The crystals were sufficiently washed with diethyl ether and dried, upon which 5.71 g (yield, 93.2%) of the trifluoroacetic acid salt of 7-[2-(2-aminothiazol-4-yl)-2-(syn)-methoxyiminoacetamido]-3-[1-(5-chloro-1,2,4-triazolyl)]methyl-Δ³-cephem-4-carboxylic acid having a melting point of 162° C. (decomp.).

IR (KBr) cm⁻¹: νC=O 1778, 1715, 1670, 1630
NMR (d₆-DMSO) δ value: 3.48(2H, bs, C₂—H), 3.93(3H, s, —OCH₃), 4.98–5.42(3H, m,

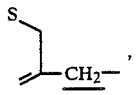,

C₆—H), 5.78(1H, dd, J=5 Hz, J=8 Hz, C₇—H), 6.91(1H, s,

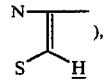), 8.02(1H, s,

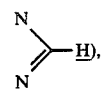), 9.74(1H, d, J=8 Hz, —CONH—)

EXAMPLE 3

The same reaction as in Example 1 or 2 was carried out to obtain the compounds shown in Table 6 in a yield of 70–90%.

TABLE 6

(syn-isomer)

| R⁵ᵃ | R⁷ | Melting point (°C.) | IR(KBr) cm⁻¹:νC=O | NMR (d₆-DMSO) δ value: |
|---|---|---|---|---|
| —CH₂OCOC(CH₃)₃ | phenyl * | 119–123 (decomp.) | 1780, 1740, 1670 | 1.15 (9H, s, —C(CH₃)₃), 3.18, 3.60 (2H, ABq, J=18Hz, C₂—H), 3.58–4.22 (2H, m, thiazoline-CH₂—), 3.93 (3H, s, —OCH₃), 5.17 (1H, d, J=5Hz, C₆—H), 5.48–6.02 (3H, m, —OCH₂O—, C₇—H), 6.92 (1H, s, aminothiazolyl), 7.21 (5H, bs, —C₆H₅), 9.85 (1H, d, J=8Hz, —CONH—) |
| —CH₂OCOC(CH₃)₃ | 1-methyltetrazolyl CH₃* | 144–146 (decomp.) | 1780, 1745, 1660 | 1.16 (9H, s, —C(CH₃)₃), 2.39 (3H, s, tetrazolyl-CH₃), 3.56 (2H, bs, C₂—H), 3.88 (3H, s, —OCH₃), 4.85–5.46 (3H, m, thiazoline-CH₂—, C₆—H), 5.52–6.01 (3H, m, —OCH₂O—, C₇—H), 6.86 (1H, s, aminothiazolyl), 7.80 (1H, s, triazolyl-H), 9.74 (1H, d, J=8Hz, —CONH—) |

TABLE 6-continued

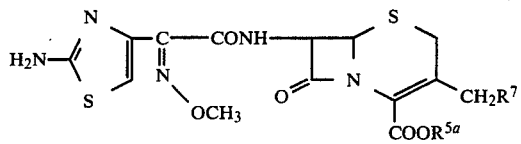

(syn-isomer)

| Compound | | Melting | IR(KBr) | |
|---|---|---|---|---|
| $R^{5a}$ | $R^7$ | point (°C.) | $cm^{-1}:\nu_{C=O}$ | NMR ($d_6$-DMSO) δ value: |
| —CH$_2$OCOC(CH$_3$)$_3$ | -N(N=CH-N=)-C(SCH$_3$)* | 135–137 (decomp.) | 1785, 1745, 1672 | 1.17 (9H, s, —C(CH$_3$)$_3$), 2.49 (3H, s, —SCH$_3$), 3.52 (2H, bs, C$_2$—H), 3.93 (3H, s, —OCH$_3$), 4.87–5.38 (3H, m, S-CH$_2$-, C$_6$—H), 5.50–6.05 (3H, m, —OCH$_2$O—, C$_7$—H), 6.92 (1H, s, N=C(S)–H), 8.50 (1H, s, N=CH-N—H), 9.80 (1H, d, J=8Hz, —CONH—) |
| —CH$_2$OCOC(CH$_3$)$_3$ | —NHCOCH$_3$ | 133–135 (decomp.) | 1780, 1740, 1680~1620 | 1.16 (9H, s, —C(CH$_3$)$_3$), 1.81 (3H, s, —COCH$_3$), 3.46 (2H, bs, C$_2$—H), 3.61–4.18 (2H, m, S-CH$_2$-), 3.80 (3H, s, —OCH$_3$), 5.05 (1H, d, J=5Hz, C$_6$—H), 5.48–6.00 (3H, m, —OCH$_2$O—, C$_7$—H), 6.66 (1H, s, N=C(S)–H), 7.12 (2H, bs, —NH$_2$), 7.78–8.09 (1H, m, —NHCO—), 9.45 (1H, d, J=8Hz, —CONH—) |
| —CH$_2$OCOC(CH$_3$)$_3$ | -N(N=CH-N=)-CH | 130–132 (decomp.) | 1780, 1745, 1665 | 1.21 (9H, s, —C(CH$_3$)$_3$), 3.50 (2H, bs, C$_2$—H), 3.90 (3H, s, —OCH$_3$), 4.88–5.30 (3H, m, S-CH$_2$-, C$_6$—H), 5.64–6.04 (3H, m, —OCH$_2$O—, C$_7$—H), 6.72 (1H, s, N=C(S)–H), 7.83 (1H, s, N=CH–H), 8.37 (1H, s, N=CH–H), 9.46 (1H, d, J=8Hz, —CONH—) |
| —CH$_2$OCOCH$_3$ | -N(N=N-N=)-C(CH$_3$) | 121–124 (decomp.) | 1780, 1745, 1670 | 2.10 (3H, s, —OCCH$_3$ (‖O)), 2.46 (3H, s, N=C(N)-CH$_3$), 3.52 (2H, bs, C$_2$—H), 3.82 (3H, s, —OCH$_3$), 5.19 (1H, d, J=5Hz, C$_6$—H), 5.59 (2H, bs, S-CH$_2$-), 5.78 (1H, dd, J=5Hz, J=8Hz, C$_7$—H), 5.83 (2H, s, —OCH$_2$O—), 6.69 (1H, s, N=C(S)–H), 7.12 (2H, bs, —NH$_2$), 9.55 (1H, d, J=8Hz, —CONH—) |

TABLE 6-continued

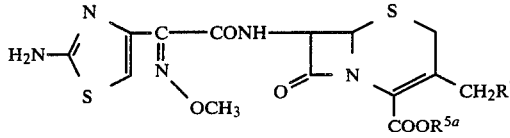

(syn-isomer)

| Compound | | Melting | IR(KBr) | |
|---|---|---|---|---|
| $R^{5a}$ | $R^7$ | point (°C.) | $cm^{-1}:\nu_{C=O}$ | NMR ($d_6$-DMSO) δ value: |
| —CHOCOC(CH$_3$)$_3$<br>  \|<br>  CH$_3$ | 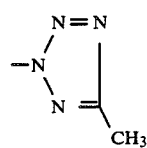 | 127–130<br>(decomp.) | 1780, 1740,<br>1675 | 1.14 (9H, s, —C(CH$_3$)$_3$), 1.48 (3H, d, J=5.5Hz, —CH—\|CH$_3$), 2.45 (3H, s, N≡C—CH$_3$), 3.48 (2H, bs, C$_2$—H), 3.82 (3H, s, —OCH$_3$), 5.19 (1H, d, J=5Hz, C$_6$—H), 5.54 (2H, bs, S—CH$_2$—), 5.83 (1H, dd, J=5Hz, J=8Hz, C$_7$—H), 6.69 (1H, s, N=\|S—H), 6.86 (1H, q, J=5.5Hz, —CH—\|CH$_3$), 7.11 (2H, bs, —NH$_2$), 9.56 (1H, d, J=8Hz, —CONH—) |
| —CH$_3$ | 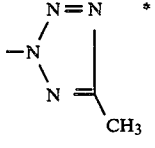 | 154<br>(decomp.) | 1785, 1730,<br>1655 | 2.48 (3H, s, N≡C—CH$_3$), 3.53 (2H, bs, C$_2$—H), 3.81 (3H, s, —COOCH$_3$), 3.96 (3H, s, —OCH$_3$), 5.23 (1H, d, J=5Hz, C$_6$—H), 5.61 (2H, bs, S—CH$_2$—), 5.83 (1H, dd, J=5Hz, J=8Hz, C$_7$—H), 6.95 (1H, s, N=\|S—H), 9.88 (1H, d, J=8Hz, —CONH—) |
| 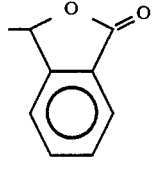 | 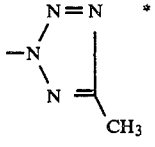 | 166–168<br>(decomp.) | 1775, 1745,<br>1665 | 2.41 (3H, s, N≡C—CH$_3$), 3.58 (2H, bs, C$_2$—H), 3.93 (3H, s, —OCH$_3$), 5.19 (1H, d, J=5Hz, C$_6$—H), 5.62 (2H, bs, S—CH$_2$—), 5.78 (1H, dd, J=5Hz, J=8Hz, C$_7$—H), 6.88 (1H, s, N=\|S—H), 7.62 (1H, s, 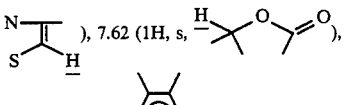), 7.67–8.00 (4H, m, ), 9.80 (1H, d, J=8Hz, —CONH—) |
| —CHOCOC(CH$_3$)$_3$<br>  \|<br>  CH$_3$ | 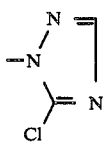 | 145–147 | 1780, 1742,<br>1670 | 1.17 (9H, s, —C(CH$_3$)$_3$), 1.52 (3H, d, J=6Hz, —CH—\|CH$_3$), 3.54 (2H, bs, C$_2$—H), 3.92 (3H, s, —OCH$_3$), 4.98–5.50 (3H, m, C$_6$—H, S—CH$_2$—), 5.87 (1H, dd, J=5Hz, J=8Hz, C$_7$—H), |

TABLE 6-continued (syn-isomer, structure shown with aminothiazole-methoxyimino-cephem core, CH2R7 at 3-position, COOR5a)

| Compound R5a | R7 | Melting point (°C.) | IR(KBr) cm⁻¹:ν$_{C=O}$ | NMR (d6-DMSO) δ value: |
|---|---|---|---|---|
| | | | | 6.85 (1H, s, thiazole-H), 6.97–7.24 (1H, m, —CH(CH3)—), 8.24 (1H, s, amidine-H), 9.78 (1H, d, J=8Hz, —CONH—) |
| —CH2OCO(CH2)3CH3 | 3-methyl-1,2,4-triazol-1-yl (N=N, —N—, CH3) | 107–108 | 1780, 1760, 1670 | 0.87 (3H, t, J=7Hz, —(CH2)3CH3), 1.0–1.7 (4H, m, —CH2CH2CH2CH3), 2.25–2.55 (2H, m, —CH2CH2CH2CH3), 2.45 (3H, s, =N—CH3), 3.33 (2H, bs, C2—H), 3.85 (3H, s, —OCH3), 5.20 (1H, d, J=5Hz, C6—H), 5.58 (2H, bs, S—CH2—), 5.73–5.97 (1H, m, C7—H), 5.88 (2H, s, —OCH2O—), 6.70 (1H, s, thiazole-H), 7.18 (2H, bs, —NH2), 9.60 (1H, d, J=9Hz, —CONH—) |
| —CH2OCOC(CH3)3 | 5-chloro-triazolyl (N=, —N—, Cl, N) | 118–122 (decomp.) | 1780, 1745, 1670 | 1.19 (9H, s, —C(CH3)3), 3.46 (2H, bs, C2—H), 3.91 (3H, s, —OCH3), 4.93–5.51 (3H, m, C6—H, S—CH2—), 5.64–6.18 (3H, m, C7—H, —OCH2O—), 6.82 (1H, s, thiazole-H), 7.31 (2H, bs, —NH2), 8.11 (1H, s, amidine-H), 9.78 (1H, d, J=8Hz, —CONH—) |
| —CHOCOC(CH3)3, CH2, CH3 | 3-methyl-triazolyl (N=N, —N—, CH3) | 140–142 (decomp.) | 1785, 1745, 1675 | — |
| —CHOCOC(CH3)3, phenyl | 3-methyl-triazolyl (N=N, —N—, CH3) | 153–157 (decomp.) | 1785, 1745, 1680 | — |
| —CHOCO-phenyl, CH3 | 3-methyl-triazolyl (N=N, —N—, CH3) | 125 (decomp.) | 1780, 1740, 1675 | — |

TABLE 6-continued

[Structure: 2-aminothiazole-methoxyimino cephalosporin core with CH₂R⁷ at 3-position and COOR⁵ᵃ]

(syn-isomer)

| Compound R⁵ᵃ | R⁷ | Melting point (°C.) | IR(KBr) cm⁻¹:ν$_{C=O}$ | NMR (d₆-DMSO) δ value: |
|---|---|---|---|---|
| —CHOCOC(CH₃)₃<br>\|<br>CH₃ | [triazole with N=N, —N, N, CH₃ substituent] | 150–160 (decomp.) | 1793, 1742, 1675 | — |
| —CHOCOC(CH₃)₃<br>\|<br>CH₃ | [pyrimidinedione: —N, N—CH₃ with two C=O] | 198–201 (decomp.) | 1780, 1740, 1680~1640 | 1.19 (9H, s, —C(CH₃)₃), 1.54 (3H, d, J=5Hz, —CH— \| CH₃ ), 3.30 (3H, s, \N—CH₃), 3.54 (2H, bs, C₂—H), 3.88 (3H, s, —OCH₃), 4.40, 5.06 (2H, ABq, J=15Hz, S—CH₂—), 5.24 (1H, d, J=5Hz, C₆—H), 5.91 (1H, dd, J=5Hz, J=8Hz, C₇—H), 6.46, 6.60 (2H, ABq, J=6Hz, H—C=C—H ), 6.80 (1H, s, thiazole-H), 7.07 (1H, q, J=5Hz, —CH— \| CH₃ ), 7.26 (2H, bs, —NH₂), 9.74 (1H, d, J=8Hz, —CONH—) |
| —CHOCOC(CH₃)₃<br>\|<br>CH₃ | [pyrimidinedione: —N, N—CH₂CH₃] | 148–150 | 1780, 1740, 1680, 1640 | 0.90–1.39 (12H, m, —C(CH₃)₃, \NCH₂CH₃), 1.52 (3H, d, J=5Hz, —CH— \| CH₃ ), 3.52 (2H, bs, C₂—H), 3.76 (2H, q, J=7Hz, \NCH₂CH₃), 3.88 (3H, s, —OCH₃), 4.38, 5.04 (2H, ABq, J=15Hz, S—CH₂—), 5.21 (1H, d, J=5Hz, C₆—H), 5.87 (1H, dd, J=5Hz, J=8Hz, C₇—H), 6.61 (2H, bs, H—C=C—H ), 6.78 (1H, s, thiazole-H), 7.04 (1H, q, J=5Hz, —CH— \| CH₃ ), 7.22 (2H, bs, —NH₂), 9.67 (1H, d, J=8Hz, —CONH—) |
| —CHOCOC(CH₃)₃<br>\|<br>CH₃ | [pyrimidinedione: —N, N—(CH₂)₄CH₃] | 139–141 (decomp.) | 1783, 1740, 1680, 1640 | 0.87 (3H, t, J=7Hz, \N(CH₂)₄CH₃), 1.18 (9H, s, —C(CH₃)₃), 1.04–1.85 (6H, m, \NCH₂(CH₂)₃CH₃), 1.53 (3H, d, J=5Hz, —CH— \| CH₃ ), 3.59 (2H, bs, C₂—H), 3.72 (2H, t, J=7Hz, |

TABLE 6-continued

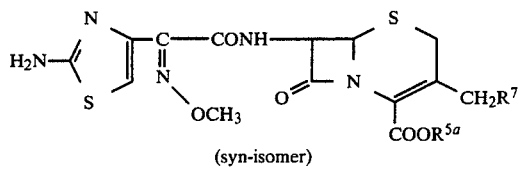

(syn-isomer)

| Compound | | Melting | IR(KBr) | |
|---|---|---|---|---|
| $R^{5a}$ | $R^7$ | point (°C.) | $cm^{-1}:\nu_{C=O}$ | NMR ($d_6$-DMSO) δ value: |
| | | | | $\diagdown$NCH$_2$(CH$_2$)$_3$CH$_3$), 3.91 (3H, s, —OCH$_3$), 4.45, 5.08 (2H, ABq, J=15Hz, S–CH$_2$–), 5.28 (1H, d, J=5Hz, C$_6$—H), 5.92 (1H, dd, J=5Hz, J=8Hz, C$_7$—H), 6.65 (2H, bs, \>C=C\<H,H), 6.85 (1H, s, N=C(S)H), 7.00 (1H, q, J=5Hz, —CH(CH$_3$)—), 9.82 (1H, d, J=8Hz, —CONH—) |
| —CHOCOC(CH$_3$)$_3$ \| CH$_3$ | [N,N′-pentyl dioxo-pyrazine ring] | 145–150 (decomp.) | 1780, 1740, 1685, 1645 | 0.87 (3H, t, J=7Hz, \>N(CH$_2$)$_5$CH$_3$), 1.03–1.79 (8H, m, \>NCH$_2$(CH$_2$)$_4$CH$_3$), 1.18 (9H, s, —C(CH$_3$)$_3$), 1.53 (3H, d, J=5Hz, —CH(CH$_3$)—), 3.60 (2H, bs, C$_2$—H), 3.72 (2H, t, J=7Hz, \>NCH$_2$(CH$_2$)$_4$CH$_3$), 3.90 (3H, s, —OCH$_3$), 4.41, 5.09 (2H, ABq, J=15 Hz, S–CH$_2$–), 5.25 (1H, d, J=5Hz, C$_6$—H), 5.90 (1H, dd, J=5Hz, J=8Hz, C$_7$—H), 6.63 (2H, bs, \>C=C\<H,H), 6.82 (1H, s, N=C(S)H), 6.98 (1H, q, J=5Hz, —CH(CH$_3$)—), 9.75 (1H, d, J=8Hz, —CONH—) |
| —CHOCOC(CH$_3$)$_3$ \| CH$_3$ | [N,N′-heptyl dioxo-pyrazine ring] | 170–172 (decomp.) | 1780, 1740, 1680, 1640 | 0.88 (3H, t, J=8Hz, \>N(CH$_2$)$_7$CH$_3$), 1.02–1.43 (21H, m, —C(CH$_3$)$_3$, \>NCH$_2$(CH$_2$)$_6$CH$_3$), 1.56 (3H, d, J=5Hz, —CH(CH$_3$)—), 3.38–3.83 (4H, m, \>NCH$_2$(CH$_2$)$_6$CH$_3$, C$_2$—H), 3.90 (3H, s, —OCH$_3$), 4.43, 5.11 (2H, ABq, |

TABLE 6-continued

[Structure: syn-isomer of cephalosporin with aminothiazole, methoxyimino, and substituents R⁷ and COOR^5a]

| Compound | | Melting point (°C.) | IR(KBr) cm⁻¹:ν_{C=O} | NMR (d₆-DMSO) δ value: |
|---|---|---|---|---|
| R^5a | R⁷ | | | |

J=15Hz, [S-CH₂]), 5.28 (1H, d, J=5Hz, C₆—H), 5.94 (1H, dd, J=5Hz, J=8Hz, C₇—H), 6.65 (2H, bs, [=CH₂]), 6.83 (1H, s, [thiazole-H]), 7.02 (1H, q, J=5Hz, —CH(CH₃)—), 7.15 (2H, bs, —NH₂), 9.70 (1H, d, J=8Hz, —CONH—)

| —CHOCOC(CH₃)₃  | [pyrimidine-dione with N—(CH₂)₁₁CH₃] | 153–158 (decomp.) | 1780, 1745, 1675, 1640 | 0.86 (3H, t, J=7Hz, NCH₂(CH₂)₁₀CH₃), 1.02–1.87 (20H, m, NCH₂(CH₂)₁₀CH₃), 1.18 (9H, s, —C(CH₃)₃), 1.52 (3H, d, J=5Hz, —CH(CH₃)—), 3.53 (2H, bs, C₂—H), 3.70 (2H, t, J=7Hz, NCH₂(CH₂)₁₀CH₃), 3.87 (3H, s, —OCH₃), 4.38, 5.03 (2H, ABq, J=15Hz, [S-CH₂]), 5.20 (1H, d, J=5Hz, C₆—H), 5.85 (1H, dd, J=5Hz, J=8Hz, C₇—H), 6.58 (2H, bs, [=CH₂]), 6.75 (1H, s, [thiazole-H]), 7.01 (1H, q, J=5Hz, —CH(CH₃)—), 9.65 (1H, d, J=8Hz, —CONH—) |
| | CH₃ | | | |

| —CH₂OCOC(CH₃)₃ | [pyrimidine-dione with N—CH₂CH₃] | 145–147 | 1780, 1740, 1675, 1640 | 1.01–1.35 (12H, m, —C(CH₃)₃, NCH₂CH₃), 3.47 (2H, bs, C₂—H), 3.70 (2H, q, J=7Hz, NCH₂CH₃), 3.78 (3H, s, —OCH₃), 4.30, 5.01 (2H, ABq, J=15Hz, [S-CH₂]), 5.14 (1H, d, J=5Hz, C₆—H), 5.67–6.06 (3H, m, —OCH₂O—, C₇—H), 6.55 (2H, bs, [=CH₂]), 6.70 (1H, s, [thiazole-H]), 7.12 (2H, bs, —NH₂), 9.52 (1H, d, J=8Hz, —CONH—) |

TABLE 6-continued

Structure (syn-isomer): 2-aminothiazole with =N-OCH3, -CONH- linked to cephem nucleus with CH2R7 at 3-position and COOR^{5a}

| Compound R^{5a} | R^7 | Melting point (°C.) | IR(KBr) cm$^{-1}$:$\nu_{C=O}$ | NMR (d$_6$-DMSO) δ value: |
|---|---|---|---|---|
| (phthalidyl group: benzofuranone-CH-O-)** | (1-ethyl-2,6-dioxo-1,2,3,6-tetrahydropyrimidin-3-yl: -N(CO)N(CH2CH3)(CH=CH)-) | * >200 | 1780, 1680, 1640 | 1.21 (3H, t, J=7Hz, NCH$_2$CH$_3$), 3.67 (2H, bs, C$_2$—H), 3.81 (2H, t, J=7Hz, NCH$_2$CH$_3$), 3.99 (3H, s, —OCH$_3$), 4.17–5.13 (5H, m, —CH$_2$—, —NH$_3^\oplus$), 5.22 (1H, d, J=5Hz, C$_6$—H), 5.83 (1H, dd, J=5Hz, J=8Hz, C$_7$—H), 6.59, 6.77 (2H, ABq, J=7Hz, CH=CH), 6.95 (0.5H, s, thiazole-H × 0.5), 7.00 (0.5H, s, thiazole-H × 0.5), 7.58–8.15 (5H, m, phthalidyl-H), 9.87 (1H, d, J=8Hz, —CONH—) |
| —(CH$_2$)$_3$CH$_3$ | (1-ethyl-2,6-dioxo-1,2,3,6-tetrahydropyrimidin-3-yl) | 139–144 (decomp.) | 1780, 1720, 1680, 1640 | 0.63–1.85 (10H, m, —OCH$_2$CH$_2$CH$_2$CH$_3$, NCH$_2$CH$_3$), 3.55 (2H, bs, C$_2$—H), 3.76 (2H, q, J=7Hz, NCH$_2$CH$_3$), 3.89 (3H, s, —OCH$_3$), 4.30 (2H, t, J=7Hz, —OCH$_2$CH$_2$CH$_3$), 4.39, 5.12 (2H, ABq, J=15Hz, —CH$_2$—), 5.25 (1H, d, J=5Hz, C$_6$—H), 5.92 (1H, dd, J=5Hz, J=8Hz, C$_7$—H), 6.68 (2H, bs, CH=CH), 6.82 (1H, s, thiazole-H), 7.28 (2H, bs, —NH$_2$), 9.79 (1H, d, J=8Hz, —CONH—) |
| —CH$_2$OCOC(CH$_3$)$_3$ | (2-oxo-2H-pyrazin-1-yl) | 134–137 (decomp.) | 1780, 1750, 1680~1650 | 1.24 (9H, s, —C(CH$_3$)$_3$), 3.53 (2H, bs, C$_2$—H), 4.06 (3H, s, —OCH$_3$), 4.70, 5.35 (2H, ABq, J=15Hz, —CH$_2$—), 5.25 (1H, d, J=5Hz, C$_6$—H), 5.98–6.48 (5H, m, —OCH$_2$O—, |

TABLE 6-continued (syn-isomer)

| Compound | | Melting point (°C.) | IR(KBr) cm$^{-1}$:ν$_{C=O}$ | NMR (d$_6$-DMSO) δ value: |
|---|---|---|---|---|
| R$^{5a}$ | R$^7$ | | | |
| | | | | C$_7$—H, —NH$_2$), 6.88 (1H, s, [thiazole-H]), 7.54, 7.70 (2H, ABq, J=5Hz, [vinyl-H]), 8.33 (1H, s, [N=CH]), 8.59 (1H, d, J=8Hz, —CONH—) (measured in CDCl$_3$) |
| —CH$_2$OCOC(CH$_3$)$_3$ | 6-methyl-3-oxo-2,3-dihydropyridazin-2-yl | 141–142 (decomp.) | 1775, 1740, 1650 | 1.24 (9H, s, —C(CH$_3$)$_3$), 2.31 (3H, s, [N=C-CH$_3$]), 3.40 (2H, bs, C$_2$—H), 3.99 (3H, s, —OCH$_3$), 5.01, 5.33 (2H, ABq, J=15Hz, [S-CH$_2$]), 5.09 (1H, d, J=5Hz, C$_6$—H), 5.61–6.14 (3H, m, —OCH$_2$O—, C$_7$—H), 6.71 (2H, bs, —NH$_2$), 6.77 (1H, s, [thiazole-H]), 6.86, 7.24 (2H, ABq, J=10Hz, [vinyl-H]), 9.34 (1H, d, J=8Hz, —CONH—) |
| —CH$_2$OCOC(CH$_3$)$_3$ | 5,5,6-trimethyl-3-oxo-2,3,4,5-tetrahydropyrazin-2-yl | 156–159 | 1775, 1740, 1670~1640 | 1.19 (9H, s, —C(CH$_3$)$_3$), 2.27 (6H, s, [C(CH$_3$)$_2$]), 3.35 (2H, bs, C$_2$—H), 3.86 (3H, s, —OCH$_3$), 5.02, 5.40 (2H, ABq, J=15Hz, [S-CH$_2$]), 5.20 (1H, d, J=5Hz, C$_6$—H), 5.70–6.14 (3H, m, C$_7$—H, —OCH$_2$O—), 6.81 (1H, s, [thiazole-H]), 7.26 (2H, m, —NH$_2$), 7.98 (1H, s, [N=CH]) |
| —CH$_2$OCOC(CH$_3$)$_3$ | 3,6-dioxo-1,2,3,6-tetrahydropyridazin-2-yl | 151–153 (decomp.) | 1780, 1745, 1660 | 1.17 (9H, s, —C(CH$_3$)$_3$), 3.43 (4H, bs, C$_2$—H, —NH$_2$), 3.85 (3H, s, —OCH$_3$), 4.75, 5.01 (2H, ABq, J=15Hz, [S-CH$_2$]), 5.16 (1H, d, J=5Hz, C$_6$—H), 5.60–6.08 (3H, m, C$_7$—H, —OCH$_2$O—), 6.77 (1H, s, [thiazole-H]), 6.89, 7.12 (2H, ABq, J=10Hz, [vinyl-H]), 9.62 (1H, d, J=8Hz, —CONH—) |

TABLE 6-continued (syn-isomer structure shown with thiazole-aminothiazole-methoxyimino-cephem core, $R^7$ at CH$_2R^7$ position and COOR$^{5a}$)

| Compound | | Melting point (°C.) | IR(KBr) cm$^{-1}$: $\nu_{C=O}$ | NMR (d$_6$-DMSO) δ value: |
|---|---|---|---|---|
| $R^{5a}$ | $R^7$ | | | |
| —CHOCOC(CH$_3$)$_3$<br>\|<br>CH$_3$ | 3-methyl-6-oxo-pyridazin-1-yl | 143–145 (decomp.) | 1780, 1740, 1655 | 1.18 (9H, s, —C(CH$_3$)$_3$), 1.53 (3H, d, J=6Hz, —CH—\|CH$_3$), 2.28 (3H, s, N=C—CH$_3$), 3.47 (4H, bs, C$_2$—H, —NH$_2$), 3.89 (3H, s, —OCH$_3$), 4.91, 5.29 (2H, ABq, J=15Hz, S—CH$_2$—), 5.22 (1H, d, J=5Hz, C$_6$—H), 5.88 (1H, dd, J=5Hz, J=8Hz, C$_7$—H), 6.92 (1H, s, thiazole-H), 6.93, 7.41 (2H, ABq, J=10Hz, CH=CH), 6.96 (1H, q, J=6Hz, —CH—\|CH$_3$), 9.74 (1H, d, J=8Hz, —CONH—) |
| —CHOCOC(CH$_3$)$_3$<br>\|<br>CH$_3$ | 6-methyl-4-oxo-pyrimidin-1-yl | 112–116 (decomp.) | 1780, 1740, 1660 | 1.23 (9H, s, —C(CH$_3$)$_3$), 1.59 (3H, d, J=5Hz, —CH—\|CH$_3$), 2.31 (3H, s, N=C—CH$_3$), 3.53 (2H, bs, C$_2$—H), 4.05 (3H, s, —OCH$_3$), 4.75, 5.23 (2H, ABq, J=15Hz, S—CH$_2$—), 5.16 (1H, d, J=5Hz, C$_6$—H), 6.02 (1H, dd, J=5Hz, J=8Hz, C$_7$—H), 6.45 (1H, s, C=CH—), 6.86 (1H, s, thiazole-H), 7.03 (1H, q, J=5Hz, —CH—\|CH$_3$), 8.45 (1H, s, N=CH—N), 8.51 (1H, d, J=8Hz, —CONH—)<br>(measured in CDCl$_3$) |
| —CHOCOC(CH$_3$)$_3$<br>\|<br>CH$_3$ | 2,5-dimethyl-6-oxo-pyrimidin-1-yl | 118–121 (decomp.) | 1780, 1740, 1660 | 1.21 (9H, s, —C(CH$_3$)$_3$), 1.58 (3H, d, J=5Hz, —CH—\|CH$_3$), 2.24 (6H, s, N=C—CH$_3$, N=C—CH$_3$), 3.33 (2H, bs, C$_2$—H), 3.98 (3H, s, —OCH$_3$), 4.94, 5.27 (2H, ABq, J=15Hz, S—CH$_2$—), 5.10 (1H, d, J=5Hz, C$_6$—H), 6.01 (1H, dd, J=5Hz, J=8Hz, C$_7$—H), |

TABLE 6-continued

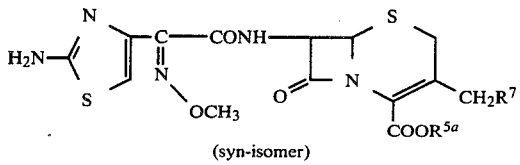

(syn-isomer)

| Compound | | Melting | IR(KBr) | |
|---|---|---|---|---|
| $R^{5a}$ | $R^7$ | point (°C.) | $cm^{-1}:\nu_{C=O}$ | NMR (d$_6$-DMSO) δ value: |
| | | | | 6.20 (1H, s, 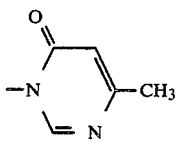), 6.75 (1H, s, 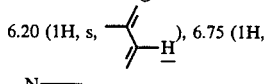), 7.04 (1H, q, J=5Hz, 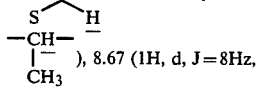), 8.67 (1H, d, J=8Hz, —CONH—) |
| —CH$_2$OCOC(CH$_3$)$_3$ | 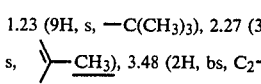 | 124–125 (decomp.) | 1780, 1745, 1680, 1670 | 1.23 (9H, s, —C(CH$_3$)$_3$), 2.27 (3H, s, 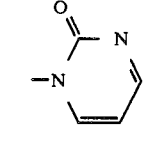), 3.48 (2H, bs, C$_2$—H), 3.98 (3H, s, —OCH$_3$), 4.68, 5.23 (2H, ABq, J=15Hz, 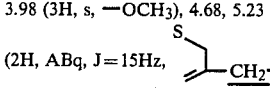), 5.15 (1H, d, J=5Hz, C$_6$—H), 5.98 (5H, bs, C$_7$—H, —OCH$_2$O—, NH$_2$—), 6.32 (1H, s, 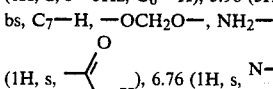), 6.76 (1H, s, 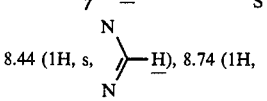), 8.44 (1H, s, 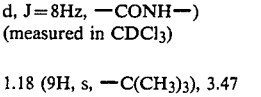), 8.74 (1H, d, J=8Hz, —CONH—) (measured in CDCl$_3$) |
| —CH$_2$OCOC(CH$_3$)$_3$ | 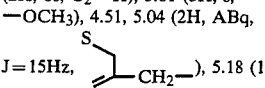 | 160–164 (decomp.) | 1785, 1750, 1665 | 1.18 (9H, s, —C(CH$_3$)$_3$), 3.47 (2H, bs, C$_2$—H), 3.81 (3H, s, —OCH$_3$), 4.51, 5.04 (2H, ABq, J=15Hz, 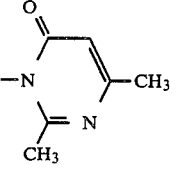), 5.18 (1H, d, J=5Hz, C$_6$—H), 5.59–6.16 (3H, m, C$_7$—H, —OCH$_2$O—), 6.30–6.64 (1H, m, 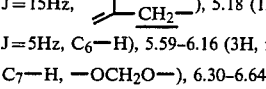), 6.75 (1H, s, 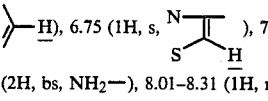), 7.18 (2H, bs, NH$_2$—), 8.01–8.31 (1H, m), 8.42–8.77 (1H, m), 9.60 (1H, d, J=8Hz, —CONH—) |
| —CH$_2$OCOC(CH$_3$)$_3$ | 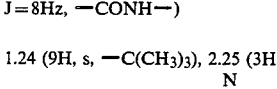 | 139–141 (decomp.) | 1780, 1740, 1690~1660 | 1.24 (9H, s, —C(CH$_3$)$_3$), 2.25 (3H, s, 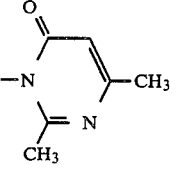), 2.44 (3H, s, 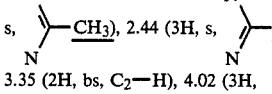), 3.35 (2H, bs, C$_2$—H), 4.02 (3H, s, —OCH$_3$), 5.13 (1H, d, J=5Hz, C$_6$—H), 5.15, 5.56 (2H, ABq, J=15Hz, 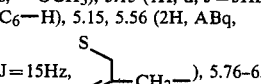), 5.76–6.21 (3H, m, C$_7$—H, —OCH$_2$O—), 6.27 (1H, s, 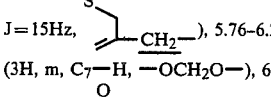), 6.83 (1H, s, 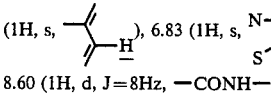), 8.60 (1H, d, J=8Hz, —CONH—) (measured in CDCl$_3$) |

TABLE 6-continued

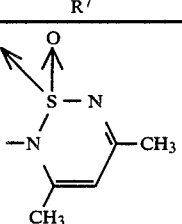

(syn-isomer)

| Compound | | Melting point (°C.) | IR(KBr) cm$^{-1}$:$\nu_{C=O}$ | NMR (d$_6$-DMSO) δ value: |
|---|---|---|---|---|
| R$^{5a}$ | R$^7$ | | | |
| —CH$_2$OCOC(CH$_3$)$_3$ | 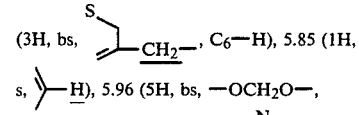 | 116–118 (decomp.) | 1780, 1745, 1670 | 1.24 (9H, s, —C(CH$_3$)$_3$), 2.25 (6H, s, —CH$_3$×2), 3.47 (2H, bs, C$_2$—H), 3.97 (3H, s, —OCH$_3$), 5.16 (3H, bs, 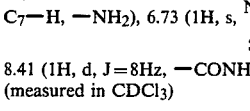, C$_6$—H), 5.85 (1H, s, 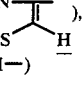), 5.96 (5H, bs, —OCH$_2$O—, C$_7$—H, —NH$_2$), 6.73 (1H, s, 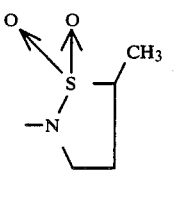), 8.41 (1H, d, J=8Hz, —CONH—) (measured in CDCl$_3$) |
| —CH$_2$OCOC(CH$_3$)$_3$ | 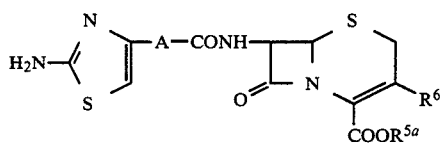 | 112–113 | 1780, 1750, 1675 | 1.23 (9H, s, —C(CH$_3$)$_3$), 1.39 (3H, d, J=7Hz, CH—CH$_3$), 1.65–3.52 (5H, m, —CH$_2$CH$_2$CH—), 3.65 (2H, bs, C$_2$—H), 4.05 (5H, s, —OCH$_3$, 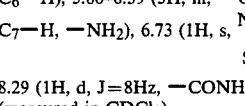), 5.18 (1H, d, J=5Hz, C$_6$—H), 5.80–6.39 (5H, m, —OCH$_2$O—, C$_7$—H, —NH$_2$), 6.73 (1H, s, 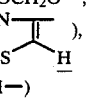), 8.29 (1H, d, J=8Hz, —CONH—) (measured in CDCl$_3$) |

Note:
*Hydrochloride (the hydrochloride was obtained in the conventional manner.)
**Diastereomer

What is claimed is:

1. A process for producing a cephalosporin represented by the formula [I] or a salt thereof:

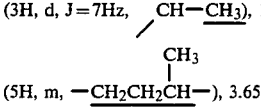 [I]

wherein R$^{5a}$ is a hydrogen atom or a carboxyl-protecting group; R$^6$ is a hydrogen atom, a halogen atom, a lower alkyl group or a group represented by the formula, —CH$_2$R$^7$ in which R$^7$ is a hydroxyl group or a C$_{1-12}$ acyloxy, carbamoyloxy, C$_{1-12}$ acylamino, phenyl, tolyl, naphthyl, indanyl, thienyl or furyl group or a heterocyclicthio group, selected from the group consisting of furylthio, thienylthio, pyrrolylthio, pyrazolylthio, imidazolylthio, thiazolylthio, isothiazolylthio, oxazolylthio, isoxazolylthio, oxadiazolylthio, triazolylthio, tetrazolylthio, thiadiazolylthio, imidazolidinylthio, imidazolinylthio, pyrrolidinylthio, pyrazolinylthio, pyrrolinylthio, thiatriazolylthio, oxatriazolylthio, indolylthio, pyridylthio, pyrimidinylthio, pyridazinylthio, pyrazinylthio, pyranylthio, piperazinylthio, piperidylthio, hexamethyleneiminothio, morpholinylthio, triazinylthio, benzothienylthio, benzofurylthio, benzoxazolylthio, benzothiazolylthio, purinylthio, isobenzofurylthio, isoindolylthio, indazolylthio, quinolizinylthio, quinolylthio and isoquinolylthio group or a heterocyclic group selected from the group consisting of 1-(1,2,3,4-tetrazolyl), 2-(1,2,3,4-tetrazolyl), 1-(1,2,3-triazolyl), 2-(1,2,3-triazolyl), 1-(1,2,4-triazolyl), 4-(1,2,4-triazolyl), 2,3-dioxo-1,2,3,4-tetrahydropyrazinyl, 3,6-dioxo-1,2,3,6-tetrahydropyridazinyl, 6-oxo-1,6-dihydropyridazinyl and 2-oxo-1,2-dihydropyrazinyl, and the above-identified groups for R$^7$ other than hydroxyl group may be substituted by, at least one substituent selected from halogen, nitro, oxo, C$_{1-14}$ alkyl, benzyl, phenethyl, 4-methylbenzyl, naphthylmethyl, phenyl, tolyl, naphthyl, indanyl, C$_{2-10}$ alkenyl, hydroxyl, C$_{1-14}$ alkoxy, C$_{1-14}$ alkylthio, cyano, amino, C$_{1-14}$ alkylamino, di-C$_{1-14}$alkylamino, C$_{1-12}$ acylamino, C$_{1-12}$ acyl, C$_{1-12}$ acyloxy, C$_{1-12}$ acyl-C$_{1-14}$alkyl, carboxyl, C$_{1-14}$ alkoxycarbonyl, C$_{1-14}$ alkoxycarbonyl-C$_{1-14}$alkyl, carbamoyl, amino-C$_{1-14}$ alkyl, N-C$_{1-14}$ alkylamino-C$_{1-14}$ alkyl, N, N-di-C$_{1-14}$-alkylamino-C$_{1-14}$ alkyl, hydroxy-C$_{1-14}$ alkyl, hydroxyimino-C$_{1-14}$ alkyl, C$_{1-14}$ alkoxy-C$_{1-14}$ alkyl, carboxy-C$_{1-14}$ alkyl, sulfo-C$_{1-14}$alkyl, sulfo, sulfamoyl-C$_{1-14}$alkyl, sulfamoyl, carbamoyl-C$_{1-14}$alkyl, carbamoyl-C$_{2-10}$-alkenyl, and N-hydroxycarbamoyl-C$_{1-14}$ alkyl groups, said thienyl and furyl group in R$^7$ being attached to the exomethylene group at the 3-position of the cephem ring through a carbon-carbon bond, and said heterocyclic group in $R^7$ being attached to the exomethylene group at the 3-position of the cephem ring through a carbon-nitrogen bond; and —A— is a methylene group of a group of the formula,

in which $R^2$ is a hydrogen atom; $C_{1-14}$alkyl, $C_{2-10}$alkenyl, $C_{2-10}$alkynyl, $C_{3-7}$cycloalkyl, $C_{5-7}$-cycloalkenyl, benzyl, phenethyl, 4-methylbenzyl, naphthylmethyl, phenyl, tolyl, naphthyl or indanyl group; a heterocyclic group selected from the group consisting of furyl, thienyl, pyrrolyl, pyrazolyl, imidazolyl, thiazolyl, isothiazolyl, oxazolyl, isoxazolyl, oxadiazolyl, triazolyl, tetrazolyl, thiadiazolyl, imidazolidinyl, imidazolinyl, pyrrolidinyl, pyrazolinyl, pyrrolinyl, thiatriazolyl, oxatriazolyl, indolyl, pyridyl, pyrimidinyl, pyridazinyl, pyrazinyl, pyranyl, piperazinyl, piperidyl, hexamethyleneimino, morpholinyl, triazinyl, benzothienyl, benzofuryl, benzoxazolyl, benzothiazolyl, purinyl, isobenzofuryl, isoindolyl, indazolyl, quinolizinyl, quinolyl and isoquinolyl; and hydroxyl-protecting group; or a group represented by the formula,

in which, $R^3$ and $R^4$, which may be the same or different, are hydroxyl, $C_{1-14}$ alkyl, benzyl, phenethyl, 4-methylbenzyl, naphthylmethyl, phenyl, tolyl, naphthyl, indanyl, $C_{1-14}$ alkoxy, benzyloxy, phenethyloxy, 4-methylbenzyloxy, naphthylmethyloxy, furyloxy or thienyloxy groups, and the above defined $C_{1-14}$ alkyl, $C_{2-10}$ alkenyl, $C_{2-10}$ alkynyl, $C_{3-7}$ cycloalkyl, $C_{5-7}$ cycloalkenyl, benzyl, phenethyl, 4-methylbenzyl, naphthyl, phenyl, tolyl, naphthylmethyl, indanyl and heterocyclic rings for $R^2$ may optionally be substituted by at least one substituent selected from the group consisting of halogen atoms, oxo, cyano, hydroxyl, $C_{1-14}$ alkoxy, amino, $C_{1-14}$alkylamino, di-$C_{1-14}$ alkylamino, the heterocyclic groups defined above in $R^2$ and groups represented by the formulas,

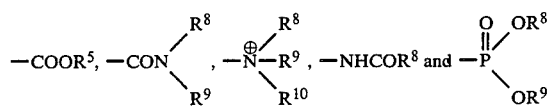

(in which $R^5$ is a carboxyl-protecting group and $R^8$, $R^9$ and $R^{10}$, which may be the same or different, are hydrogen atoms or $C_{1-14}$ alkyl, benzyl, phenethyl, 4-methylbenzyl, naphthylmethyl, phenyl, tolyl, naphthyl or indanyl groups), and the bond represents a syn or anti-isomer or a mixture thereof, which comprises reacting a compound represented by the formula [II]:

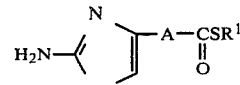

wherein —A— has the same meaning as defined above, and $R^1$ is an unsubstituted $C_{1-14}$ alkyl or phenyl group, with a compound represented by the formula [III]:

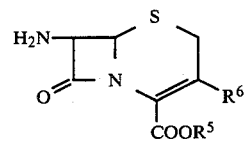

wherein $R^5$ and $R^6$ have the same meanings as defined above, in the presence of boron trifluoride or a complex compound thereof, and in the presence of an organic solvent, and then, if desired, removing the carboxyl-protecting group or converting the product to a salt.

2. A process according to claim 1, wherein $R^1$ is an unsubstituted $C_{1-14}$ alkyl group.

3. A process according to claim 1, wherein $R^1$ is an unsubstituted phenyl group.

4. A process according to any one of claims 1 to 3, wherein —A— is a group represented by the formula,

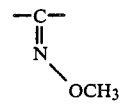

(syn isomer).

5. A process according to any one of claims 1 to 4, wherein $R^6$ is the group of the formula —$CH_2R^7$ in which $R^7$ has the same meaning as defined in claim 1.

6. A process according to claim 1, wherein $R^7$ is a $C_{1-12}$ acyloxy, 2-(1,2,3,4-tetrazolyl), 1-(1,2,4-triazolyl), tetrazolylthio, phenyl or $C_{1-12}$ acylamino group which may optionally be substituted by a halogen atom or a $C_{1-5}$ alkyl or $C_{1-5}$ alkylthio group.

7. A process according to claim 1, wherein the compound is pivaloyloxymethyl 7-[2-(2-aminothiazol-4-yl)-2-(syn)-methoxyiminoacetamido]-3-[2-(5-methyl-1,2,3,4-tetrazolyl)$\Delta^3$-methyl-$\Delta^3$-cephem-4-carboxylate or a salt thereof.

8. A process according to any one of claims 1 to 4 and 5 to 7, wherein the reaction is effected at a temperature of 0° to 100° C.

* * * * *